US011484292B2

(12) United States Patent
Tanaka

(10) Patent No.: US 11,484,292 B2
(45) Date of Patent: Nov. 1, 2022

(54) ULTRASOUND SIGNAL PROCESSING DEVICE THAT USES SYNTHETIC APERTURE METHOD AND DELAY AND SUM METHOD

(71) Applicant: Konica Minolta, Inc., Tokyo (JP)

(72) Inventor: Ryuichiro Tanaka, Kyoto-fu (JP)

(73) Assignee: KONICA MINOLTA, INC., Tokyo (JP)

( * ) Notice: Subject to any disclaimer, the term of this patent is extended or adjusted under 35 U.S.C. 154(b) by 172 days.

(21) Appl. No.: 16/507,793

(22) Filed: Jul. 10, 2019

(65) Prior Publication Data

US 2020/0046323 A1 Feb. 13, 2020

(30) Foreign Application Priority Data

Aug. 10, 2018 (JP) .............................. JP2018-151742

(51) Int. Cl.
*A61B 8/08* (2006.01)
*A61B 8/14* (2006.01)
*A61B 8/00* (2006.01)

(52) U.S. Cl.
CPC ............ *A61B 8/5207* (2013.01); *A61B 8/145* (2013.01); *A61B 8/461* (2013.01)

(58) Field of Classification Search
CPC ....... A61B 8/5207; A61B 8/145; A61B 8/461; A61B 8/54; G01S 15/8997; G01S 7/52085
See application file for complete search history.

(56) References Cited

U.S. PATENT DOCUMENTS 5,873,829 A * 2/1999 Kamiyama .......... A61B 8/5284
600/458
9,364,152 B2 * 6/2016 Oikawa ............... G01S 15/8945
(Continued)

FOREIGN PATENT DOCUMENTS

JP 2000126176 A 10/2001
JP 2009112813 A 5/2009
(Continued)

OTHER PUBLICATIONS

Masayasu Itou, Takashi Mochizuki, "Ultrasound Diagnostic Equipment", Corona Publishing Co., Ltd, Aug. 26, 2002, pp. 42-45, with partial English translation.

(Continued)

*Primary Examiner* — Oommen Jacob
*Assistant Examiner* — Nyrobi Celestine
(74) *Attorney, Agent, or Firm* — Lucas & Mercanti, LLP

(57) ABSTRACT

A reception beamformer 140 includes a delay-and-sum unit 142 that performs delay-and-sum processing with respect to reception signal sequences from multiple channels based on reflected ultrasound to calculate acoustic line signal line data. The delay-and-sum unit 142, in first reception beamforming processing, synthesizes the acoustic line signal line data calculated in the delay-and-sum processing by summing acoustic line signals associated with the observation points having the same positions, and, in the second reception beamforming processing, outputs the acoustic line signal data calculated in the delay-and-sum processing as is. Time taken by the delay-and-sum unit 142 to generate the acoustic line signal line data per set of acoustic line signal line data is equal or approximately equal in the first reception beamforming processing and the second reception beamforming processing.

13 Claims, 20 Drawing Sheets

(56) References Cited

U.S. PATENT DOCUMENTS

| | | | |
|---|---|---|---|
| 2012/0044785 A1* | 2/2012 | Yoda | G01S 15/8915 367/92 |
| 2015/0073277 A1* | 3/2015 | Hayashi | G10K 11/346 600/447 |
| 2015/0297183 A1* | 10/2015 | Freeman | G01S 15/8927 600/459 |
| 2016/0011305 A1* | 1/2016 | Koptenko | G01S 7/52047 367/7 |
| 2016/0120503 A1* | 5/2016 | Tsushima | A61B 8/5207 367/7 |
| 2016/0157827 A1* | 6/2016 | Kristoffersen | A61B 8/4494 600/447 |
| 2017/0042510 A1* | 2/2017 | Ikeda | A61B 8/14 |
| 2017/0209123 A1 | 7/2017 | Takano et al. | |
| 2017/0238908 A1* | 8/2017 | Hisatsu | A61B 8/5207 |
| 2017/0360400 A1* | 12/2017 | Kaald | A61B 8/5207 |
| 2019/0072671 A1* | 3/2019 | Nikolov | G01S 7/52046 |

FOREIGN PATENT DOCUMENTS

| | | |
|---|---|---|
| JP | 4495430 B2 | 7/2010 |
| JP | 2018110784 A | 7/2018 |
| WO | 2016009544 A1 | 1/2016 |

OTHER PUBLICATIONS

S.I.Nikolov, J.A.Jersen, "Virtual ultrasound sources in high resolution ultrasound imaging", in Proc, SPIE—Progress in biomedical optics and imaging, vol. 3, 2002, p. 395-405.

\* cited by examiner

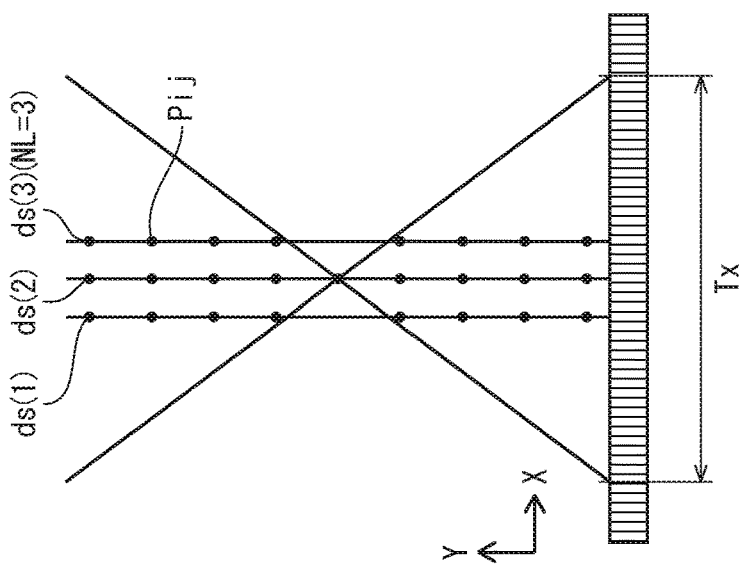
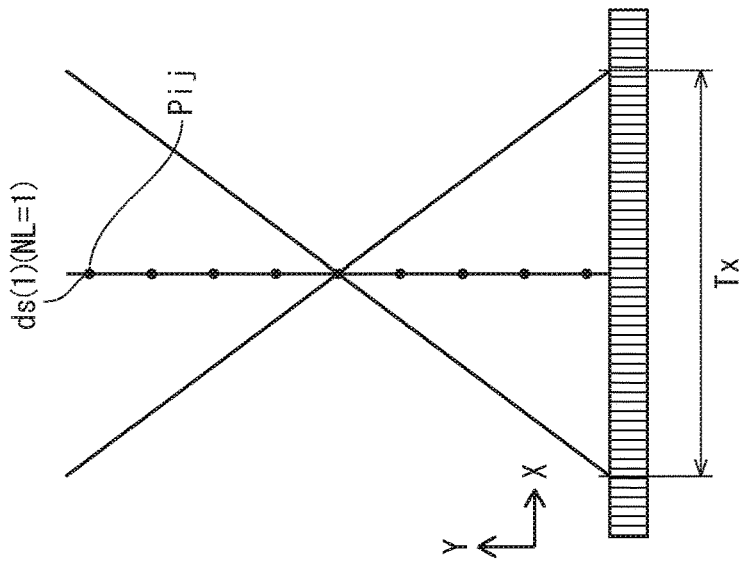
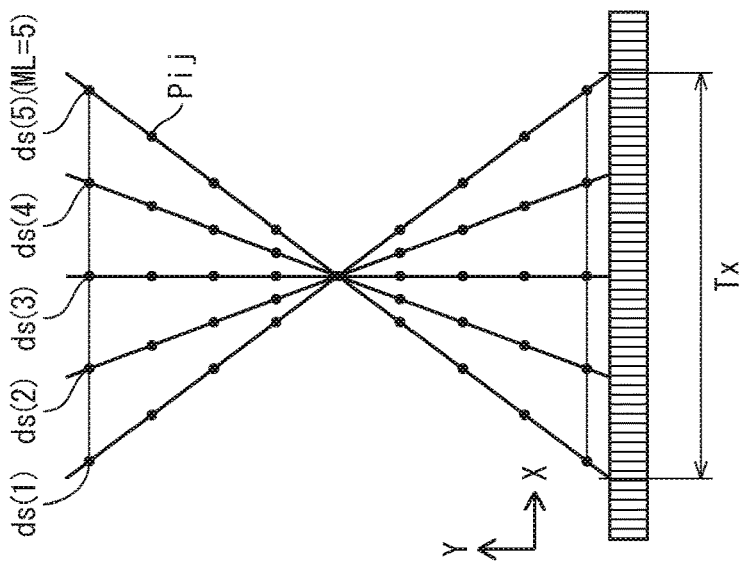

ULTRASOUND SIGNAL PROCESSING DEVICE THAT USES SYNTHETIC APERTURE METHOD AND DELAY AND SUM METHOD

CROSS REFERENCE TO RELATED APPLICATION

This application claims priority to Japanese Patent Application No. 2018-151742 filed Aug. 10, 2018, the contents of which are hereby incorporated by reference in their entirety.

BACKGROUND

Technical Field

The present disclosure relates to ultrasound signal processing devices and ultrasound diagnostic devices using same, and in particular to reception beamforming processing in ultrasound signal processing devices.

Description of the Related Art

An ultrasound diagnostic device transmits ultrasound to the inside of a subject from an ultrasound probe, receives reflected waves of ultrasound generated from differences in acoustic impedance of tissue in the subject, and generates and displays an ultrasound tomographic image indicating shapes of the tissue in the subject, based on obtained electric signals.

In conventional ultrasound diagnostic devices, delay-and-sum methods are used as reception beamforming methods based on received reflected waves (for example, see "Ultrasound Diagnostic Equipment", T. Ito and M. Tsuyoshi, Corona Publishing Co. Ltd, Aug. 26, 2002, pp 42-45). According to this method, an ultrasound beam is transmitted from a plurality of transducers to focus at a certain depth in a subject and generate an acoustic line signal on a central axis of the ultrasound beam.

As a method for obtaining a high spatial resolution, high-quality image in a region other than in close vicinity to a transmission focal point, a reception beamforming method using a synthetic aperture method has been proposed (for example, see "Virtual Ultrasound Sources in High Resolution Ultrasound Imaging", S. I. Nikolov and J. A. Jensen, SPIE—Progress in Biomedical Optics and Imaging, vol. 3, 2002, pp 395-405). According to the synthetic aperture method it is possible to generate acoustic line signals for an entirety of an ultrasound primary irradiation region that includes the close vicinity of a transmission focal point for one ultrasound transmission, by performing a delay control that takes into account both travel time to an observation point according to ultrasound transmission propagation paths and arrival times of reflected waves to transducers via the propagation paths. Further, according to the synthetic aperture method, spatial resolution and signal-to-noise ratio can be improved by superimposing a plurality of acoustic line signals for the same observation point obtained from a plurality of ultrasound transmissions. On the other hand, according to the synthetic aperture method, the number of observation points in a target area for which an acoustic line signal is generated by one ultrasound transmission increases and synthesis processing is performed superposing acoustic line signals with respect to one observation point obtained from multiple ultrasound transmissions and receptions, and therefore, when compared to a delay-and-sum method, expanded memory capacity for storing acoustic line signals is required and expanded data transmission capability is required.

As described above, reception beamforming methods in ultrasound diagnosis include delay-and-sum beamforming that has a small calculation load and synthetic aperture beamforming that has a large calculation load but excellent image quality. Both methods are functionally complementary and therefore there is a perceived need to implement both functions from the viewpoint of functional compatibility. For example, JP 2000-126176 proposed an ultrasound diagnostic device in which, after a signal obtained by a mechanically scanning ultrasound probe is subjected to multiple echo cancellation processing by a delay-and-sum unit, synthetic aperture processing is performed by the same delay-and-sum unit, and that an electronic operation type of ultrasound probe is connected to the ultrasound diagnostic device, and a delay-and-sum operation is performed with respect to signals obtained by the ultrasound probe by the delay-and-sum unit.

SUMMARY

An ultrasound signal processing device pertaining to one aspect of the present disclosure is an ultrasound signal processing device comprising ultrasound signal processing circuitry, the ultrasound signal processing circuitry comprising a reception beamformer that executes processing selected from first reception beamforming processing and second reception beamforming processing. The first reception beamforming processing includes generating, for each transmission event, a set of acoustic line signal line data including acoustic line signals associated with observation points where a portion of the observation points associated with one set have a same position as a portion of the observation points associated with another set, and synthesizing acoustic line signal line data by summing acoustic line signals that are associated with the observation points having same positions. The second reception beamforming processing includes generating, for each transmission event, a set of acoustic line signal line data including one or more acoustic line signals associated with the observation points, where positions of the observation points are different for each transmission event. Numbers of lines of the acoustic line signals generated per transmission event are different between the first reception beamforming processing and the second reception beamforming processing, and the reception beamformer includes a delay-and-sum unit that performs delay-and-sum processing with respect to reception signal sequences from multiple channels based on reflected ultrasound to calculate the acoustic line signal line data. The delay-and-sum unit, in the first reception beamforming processing, synthesizes the acoustic line signal line data calculated in the delay-and-sum processing by summing the acoustic line signals associated with the observation points having the same positions, and in the second reception beamforming processing, outputs the acoustic line signal data calculated in the delay-and-sum processing as is. Time taken by the delay-and-sum unit to generate the acoustic line signal line data per set of acoustic line signal line data is equal or approximately equal in the first reception beamforming processing and the second reception beamforming processing.

BRIEF DESCRIPTION OF DRAWINGS

These and other objects, advantages, and features of the technology pertaining to the present disclosure will become apparent from the following description thereof taken in conjunction with the accompanying drawings, which illustrate at least one embodiment of the technology pertaining to the present disclosure.

FIG. 8A is a schematic diagram illustrating an example of positions of observation points Pij for acquiring acoustic line signals to generate line data ds(q) in the first reception beamforming processing, and FIG. 8B and FIG. 8C are schematic diagrams illustrating examples of positions of observation points Pij for acquiring acoustic line signals to generate line data ds(q) in a second reception beamforming processing.

DETAILED DESCRIPTION

Developments Leading to Embodiments

According to a conventional ultrasound diagnostic device, when a reception beamforming circuit is structured to simply implement both a delay-and-sum beamforming function and a synthetic aperture beamforming function, there is a technical problem that in a simple implementation transfer rates between circuit modules are made different, interface specifications between circuit modules in the reception beamforming circuit and required specifications of circuit modules in subsequent stages become high, and therefore hardware costs of the reception beamforming circuit become high.

Further, in JP 2000-126176, there is no description that transfer rates are different between performing delay-and-sum beamforming processing and synthetic aperture beamforming processing.

The present disclosure is made in view of the above technical problems, and describes a structure in which transfer rates between circuit modules are equal or approximately equal between the first reception beamforming processing by a synthetic aperture method and the second reception beamforming processing by a simple delay-and-sum method. Thus, an object of the present disclosure is to provide an ultrasound signal processing device including a reception beamforming circuit inexpensively implementing both a delay-and-sum beamforming processing function and a synthetic aperture beamforming processing function, and an ultrasound diagnostic device including same.

Embodiment 1

<Overall Configuration>

The following is a description of an ultrasound diagnostic device 100 pertaining to Embodiment 1, described with reference to the drawings.

Figure 1:
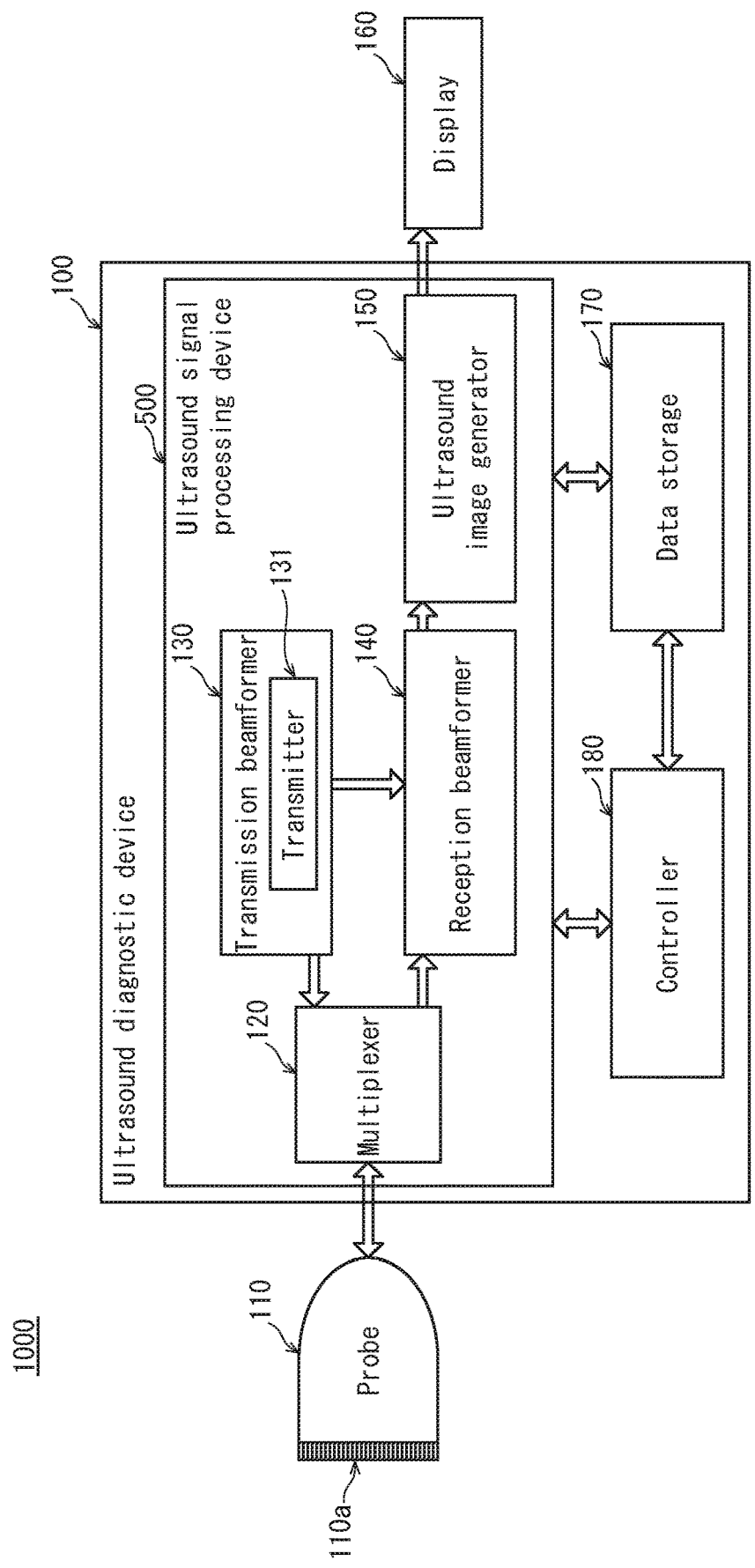
FIG. 1 is a function block diagram of an ultrasound diagnostic device 100 pertaining to Embodiment 1.

FIG. 1 is a function block diagram of an ultrasound diagnostic system 1000 pertaining to Embodiment 1. In FIG. 1, the ultrasound diagnostic system 1000 includes a probe 110 that has transducers 110a that transmit ultrasound towards a subject and receive reflected waves, the ultrasound diagnostic device 100 that causes the probe 110 to transmit and receive ultrasound and generates ultrasound images based on output signals from the probe 110, and a display 160 that displays an ultrasound image on a screen. The probe 110 and the display 160 are each connectable to the ultrasound diagnostic device 100.

<Configuration of Ultrasound Diagnostic Device 100>

The ultrasound diagnostic device 100 includes a multiplexer 120 for securing input and output for each transducer used in transmission and reception among the transducers 110a of the probe 110, a transmission beamformer 130 that controls timing of high voltage application to the transducers 110a of the probe 110 for performing ultrasound transmission, and a reception beamformer 140 that amplifies, A/D converts, and performs reception beamforming on electric signals obtained by the transducers 110a based on reflected ultrasound received by the probe 110, in order to generate acoustic line signals (delay-and-sum data (DAS data)). Further, the ultrasound diagnostic device 100 includes an ultrasound image generator 150 that generates ultrasound images (B mode images) based on output signals from the reception beamformer 140, a data storage 170 that stores ultrasound images output by the ultrasound image generator 150, and a controller 180 that controls each element. Among these elements, the multiplexer 120, the transmission beamformer 130, the reception beamformer 140, and the ultrasound image generator 150 constitute an ultrasound signal processing device 500.

Elements of the ultrasound diagnostic device 100, for example the multiplexer 120, the transmission beamformer 130, the reception beamformer 140, the ultrasound image generator 150, and the controller 180 are each implemented as a hardware circuit such as a field programmable gate array (FPGA), an application specific integrated circuit (ASIC), or the like. Alternatively, these elements may be implemented through software and a programmable device such as a processor. As a processor, a central processing unit (CPU) or a graphics processing unit (GPU) can be used, and in the case of a GPU may be referred to as general-purpose computing on a graphics processing unit (GPGPU). These elements can each be a single circuit component or an assembly of circuit components. Further, a plurality of elements can be combined into a single circuit component or can be an aggregate of a plurality of circuit components.

The data storage 170 is a computer-readable storage medium, and may be a flexible disk, a hard disk, magneto-optical (MO), a digital versatile disc (DVD), digital versatile disc random access memory (DVD-RAM), a Blu-ray Disc (BD), semiconductor memory, or the like. Further, the data storage 170 may be a storage device that is external and connectable to the ultrasound diagnostic device 100.

<Configuration of Elements of Ultrasound Diagnostic Device 100>

The ultrasound diagnostic device 100 pertaining to Embodiment 1 is characterized by the transmission beamformer 130 that causes ultrasound beam transmission from the transducers 110a of the probe 110 and the reception beamformer 140 that performs operations on electric signals obtained from ultrasound reflections received by the probe 110 in order to generate acoustic line signals for generating an ultrasound image. Thus, the present description primarily describes configuration and function of the transmission beamformer 130 and the reception beamformer 140. Note that configuration of the ultrasound diagnostic device 100 other than that of the transmission beamformer 130 and the reception beamformer 140 may be the same as that used in a known ultrasound diagnostic device, and a beamformer of a known ultrasound diagnostic device may be replaced by a beamformer pertaining to the present embodiment.

The following is a description of the transmission beamformer 130 and the reception beamformer 140.

1. Transmission Beamformer 130

The transmission beamformer 130 is connected to the probe 110 via the multiplexer 120 and controls timing of high voltage application to each of a plurality of transducers included in a transmission aperture Tx made up of all or some of the N (where N is a natural number and 2 or more) transducers 110a of the probe 110 in order to perform ultrasound transmission from the probe 110. The transmission beamformer 130 includes a transmitter 131.

Based on a transmission control signal from the controller 180, the transmitter 131 performs transmission processing supplying a pulsed transmit signal to each transducer included in the transmission aperture Tx among the transducers 110a of the probe 110, in order to cause transmission of an ultrasound beam. More specifically, the transmitter 131 includes, for example, a clock generator circuit, a pulse generator circuit, and a delay circuit. A clock generator circuit is a circuit that generates a clock signal for determining transmission timing of an ultrasound beam. A pulse generator circuit is a circuit for generating a pulse signal that drives a transducer. A delay circuit is a circuit for setting a delay time for each transducer for ultrasound beam transmission timing, delaying ultrasound beam transmission by the delay time in order to perform ultrasound beamforming.

The transmitter 131 repeatedly transmits ultrasound while shifting the transmission aperture Tx in the array direction by a movement pitch Mp (where Mp is a natural number) for each ultrasound transmission, performing ultrasound transmission from all the transducers 110a of the probe 110. According to the present embodiment, the movement pitch Mp is equivalent to one transducer, and therefore the transmission aperture Tx shifts by one transducer every ultrasound transmission. The movement pitch Mp is not limited to being equivalent to one transducer and may be equivalent to two or more transducers. Information indicating positions of transducers included in the transmission aperture Tx is outputted to the data storage 170 via the controller 180. For example, if the number N of the transducers 110a of the probe 110 is 192, a number of transducers that constitute the transmission aperture Tx may be selected from 20 to 100, for example, and may be shifted by one transducer per ultrasound transmission, for example. Hereinafter, ultrasound transmission performed from a given transmission aperture Tx by the transmitter 131 may be referred to as a "transmission event".

Figure 2:
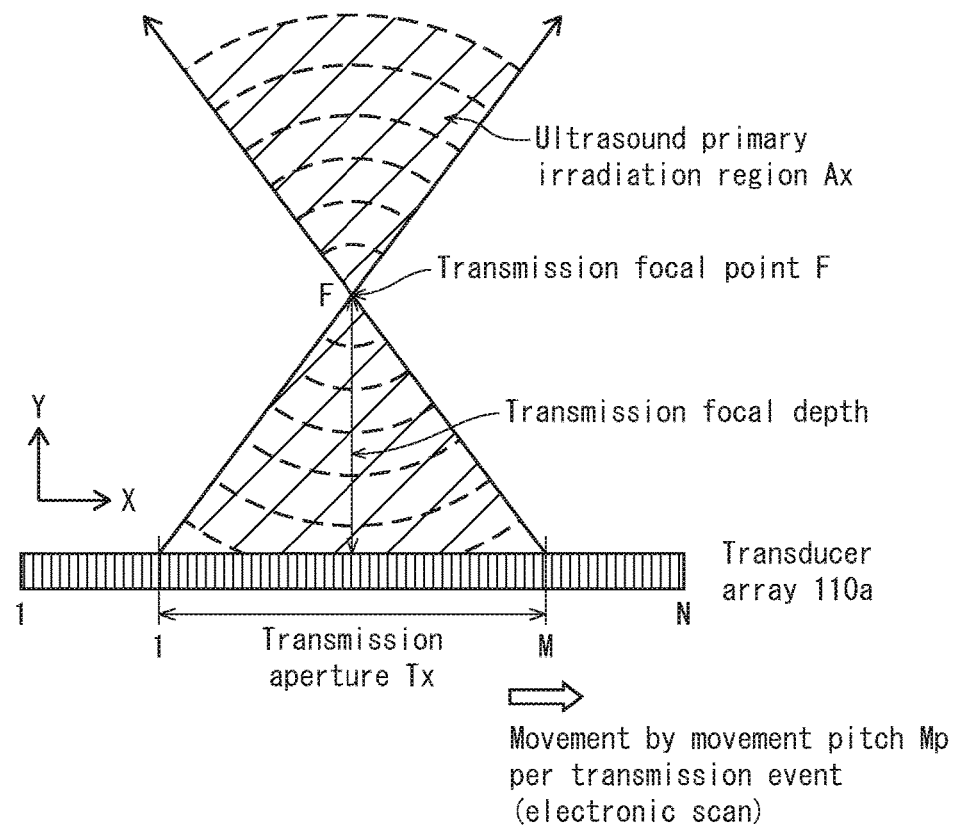
FIG. 2 is a diagram illustrating propagation paths of transmitted ultrasound beams according to a transmission beamformer 130 pertaining to Embodiment 1.

FIG. 2 is a schematic diagram illustrating propagation paths of ultrasound transmission according to the transmission beamformer 130. In a given transmission event, an array of M (where M is a natural number) transducers (transmission transducer array) included in the N transducers 110a arranged in an array contributing to ultrasound transmission is illustrated as the transmission aperture Tx. Further, array length of the transmission aperture Tx may be referred to as transmission aperture length. Further, the movement pitch Mp of the transmission transducer array each transmission event is less than the number M of the transducers included in the transmission transducer array.

In the transmission beamformer 130, transmission timing of each transducer is controlled so that the more central a transducer is in the transmission aperture Tx, the more transmission timing is delayed. As a result, a wavefront of an ultrasound transmission wave transmitted from the transducer array in the transmission aperture Tx is focused (converges) at a transmission focal point F at a focal depth in a subject. Focal depth of the transmission focal point F can be set arbitrarily. Here, the focal depth is the depth at which an ultrasound transmission wave reaches maximum convergence in an azimuth direction of the transducers (x direction in FIG. 2), that is, the depth at which the width of an ultrasound beam in the x direction is narrowest, and the transmission focal point F is a central position in the x direction of the ultrasound beam at the focal depth. However, the focal depth is constant during multiple transmission events pertaining to one frame. That is, a relationship between the transmission aperture Tx and the transmission focal point F relative to each other does not change in a plurality of transmission events pertaining to one frame. A wavefront converging at the transmission focal point F diffuses again and an ultrasound transmission wave propagates in an hourglass-shaped space bounded by two straight lines intersecting at the transmission focal point F with the transmission aperture Tx as a base. That is, an ultrasound wave radiated at the transmission aperture Tx propagates such that it gradually reduces in width in space (horizontal axis in the drawings) to a minimum width at the transmission focal point F, then as it progresses deeper (upwards in the drawings), it diffuses as the width increases. An area of this hourglass shape is an ultrasound primary irradiation region Ax.

2. Reception Beamformer 140 Configuration 2.1. Overall Configuration

The reception beamformer 140 generates acoustic line signals from electrical signals obtained by the transducers 110a, based on reflected ultrasound received by the probe 110.

As described above, in ultrasound diagnosis, beamforming methods include delay-and-sum beamforming that has a small calculation load and synthetic aperture beamforming that has a large calculation load but excellent image quality, and both methods are functionally complementary and therefore there is a need to implement both functions from the view of functional compatibility. The reception beamformer 140 implements a synthetic aperture beamforming method (also referred to as "first reception beamforming method") and a delay-and-sum beamforming method (also referred to as "second reception beamforming method"), and can selectively execute either beamforming method based on various operation conditions in ultrasound measurement.

Figure 3:
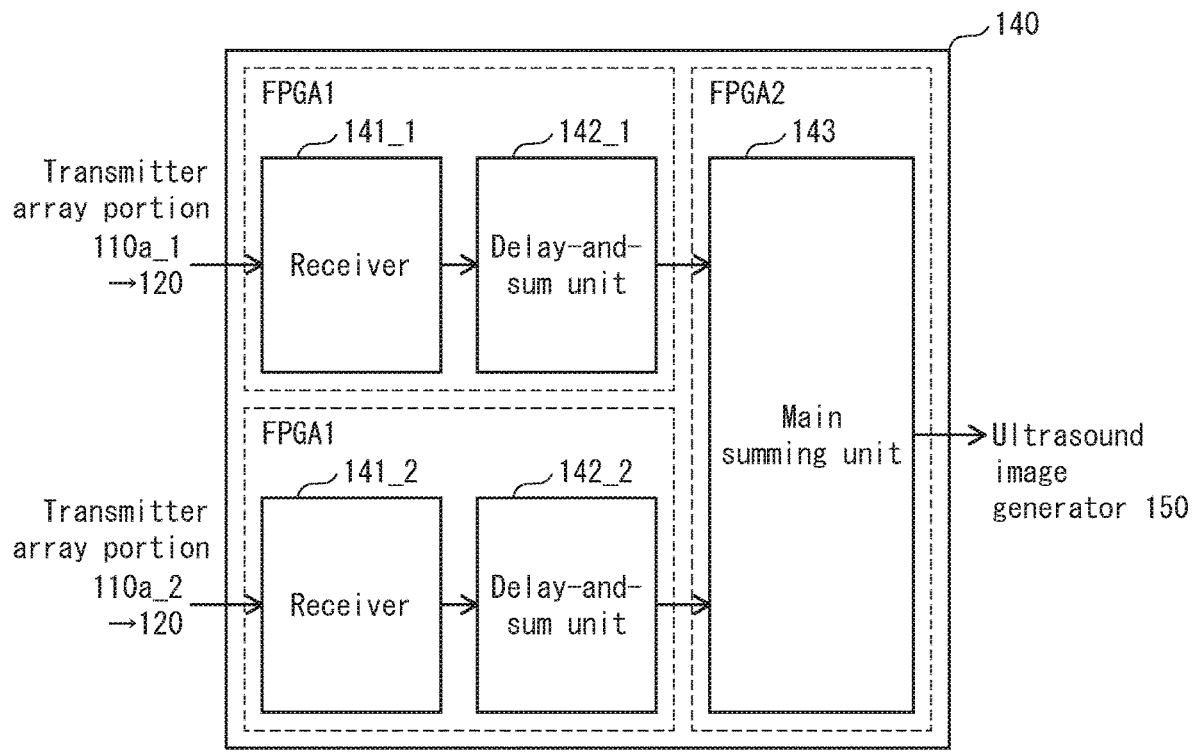
FIG. 3 is a function block diagram of a reception beamformer 140 pertaining to Embodiment 1.

Here, "acoustic line signals" are signals after delay-and-sum processing with respect to a given observation point. Delay-and-sum processing is described in more detail later. FIG. 3 is a function block diagram illustrating configuration of the transmission beamformer 140. The reception beamformer 140 pertaining to the present disclosure executes a program of the ultrasound signal processing method pertaining to the present disclosure on an FPGA based on input of an operation condition obtained from an operation input unit (not illustrated) such as a keyboard or mouse via the controller 180, to generate acoustic line signals as input of electrical signals based on reflected ultrasound from the probe 110, and outputs same to the ultrasound image generator 150.

As illustrated in FIG. 3, the reception beamformer 140 includes two receivers 141_1, 141_2 that receive electric signals based on reflected ultrasound received by the probes 110 and generate reception signal sequences, two delay-and-sum units 142_1, 142_2 that execute delay-and-sum processing on multiple channel reception signal sequences to generate acoustic line signal line data, and a main summing unit 143 that sums acoustic line signal line data outputted from the delay-and-sum units 142_1, 142_2 and outputs to the ultrasound image generator 150. For example, according to the present embodiment, the reception beamformer 140 divides a transducer array (110a) consisting of 192 of the transducers 110a into two partial transducer arrays 110a_1, 110a_2 each including 96 of the transducers 110a and includes the receivers 141_1, 141_2 (also referred to as receivers 141) that each generate a reception signal sequence for each block of the transducers 101a in a partial transducer array, the delay-and-sum units 142_1, 142_2 (also referred to as delay-and-sum units 142) that each generate an acoustic line signal for each block, and the main summing unit 143. However, the number of blocks into which the transducers 101a are divided is not limited to the above example, and may be 4, 6, 8, 16, or the like.

The receiver 141_1 and the delay-and-sum unit 142_1 corresponding to a partial transducer array block are part of a same circuit and are included in an FPGA 1, the receiver 141_2 and the delay-and-sum unit 142_2 corresponding to a partial transducer array block are part of a same circuit and are included in an FPGA 1, while the main summing unit 143 is included in an FPGA 2 that is different from the two FPGA 1. Thus, the reception beamformer 140 includes two FPGA 1 arranged in parallel and one subsequent FPGA 2.

2.2. Configuration of Each Element

Figure 4:
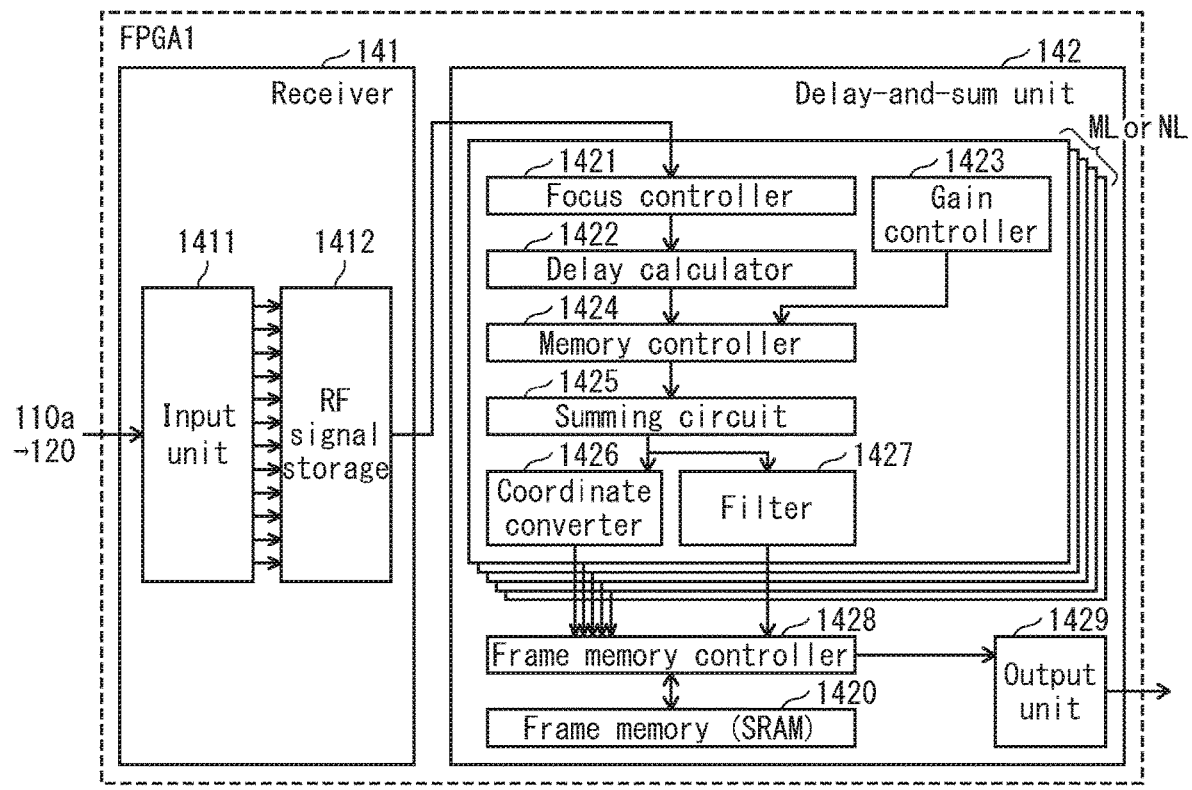
FIG. 4 is a function block diagram illustrating a receiver 141 and a delay-and-sum unit 142.
Figure 5:
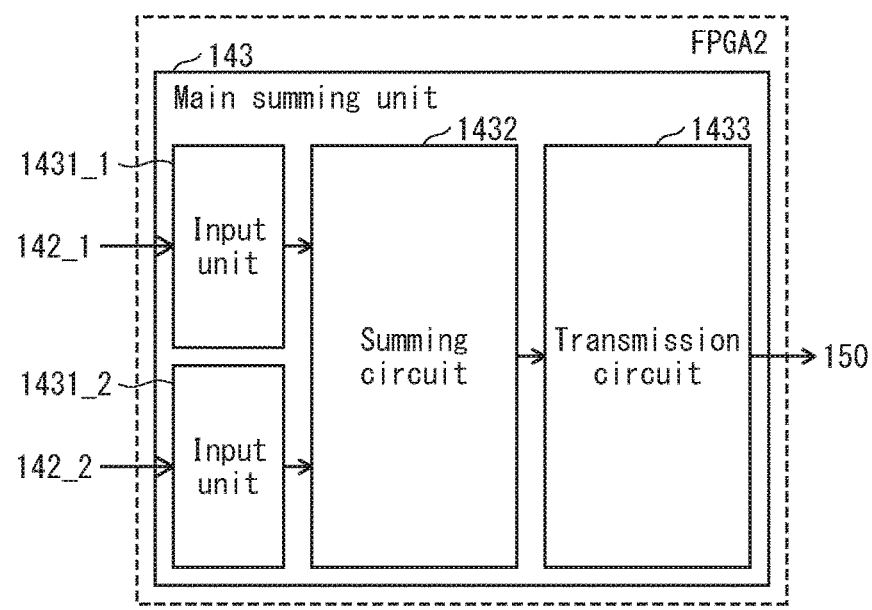
FIG. 5 is a function block diagram illustrating a main summing unit 143.

The following describes configuration of elements of the reception beamformer 140. FIG. 4 is a function block diagram illustrating configuration of the receiver 141 and the delay-and-sum unit 142 of the FPGA 1. FIG. 5 is a function block diagram illustrating configuration of the main summing unit 143 of the FPGA 2.

(1) Receiver 141

The receiver 141 is connected to the probe 110 via the multiplexer 120, and is a circuit that generates radio frequency (RF) signals by amplifying and analogue-digital (AD) converting electrical signals obtained from reception of reflected ultrasound by the probe 110 corresponding to a transmission event. The receiver 141 includes an input unit 1411 and an RF signal storage 1412 that is a semiconductor memory. The input unit 1411 generates RF signals in chronological order in an order of transmission events and stores the RF signals in the RF signal storage 1412.

Here, an RF signal is a digital signal obtained by AD conversion of an electrical signal converted from reflected ultrasound received by a transducer and is composed of a series of signals that are continuous in a transmission direction (depth direction of subject) of ultrasound received by a transducer.

Figures 6A, 6B:
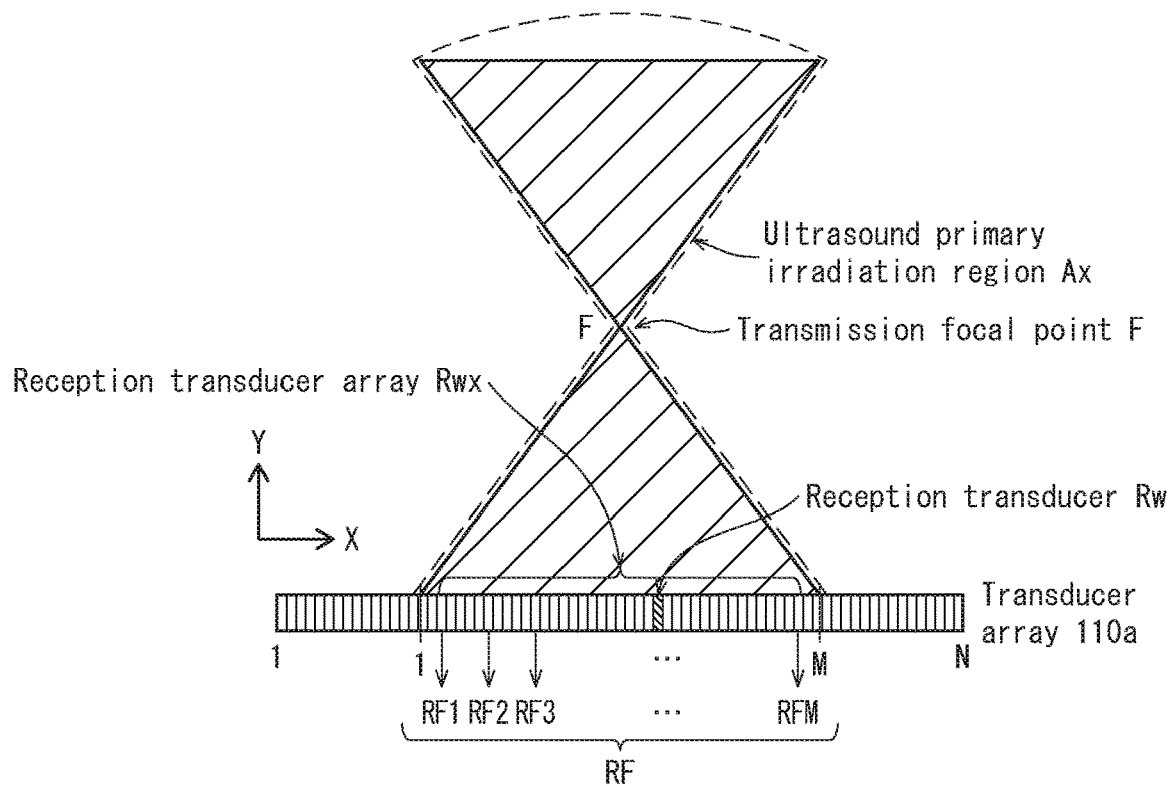
FIG. 6A is a schematic diagram illustrating generation of an RF signal sequence based on reflected ultrasound from an ultrasound primary irradiation region Ax.
FIG. 6B is a schematic diagram illustrating correspondence between RF signal sequences in a receiver 141 and addresses of an RF signal storage 1412.

FIG. 6A is a schematic diagram illustrating RF signal sequence generation based on reflected ultrasound from the ultrasound primary irradiation region Ax. In a transmission event, as stated above, the transmitter 131 causes each transducer included in the transmission aperture Tx among the transducers 110a of the probe 110 to transmit an ultrasound beam. Further, the transmitter 131 repeatedly transmits ultrasound while shifting the transmission aperture Tx in the array direction by the movement pitch Mp, corresponding to transmission events, thereby performing ultrasound transmission from all N transducers 110a of the probe 110.

The receiver 141, as illustrated in FIG. 6A, generates an RF signal sequence for each transducer, based on reflected ultrasound obtained from the ultrasound primary irradiation region Ax of the subject by each transducer corresponding to part or all of the transducers 110a of the probe 110, corresponding to a transmission event. A transducer receiving reflected ultrasound may be referred to as a reception transducer Rw, and an array of reception transducers Rw is a reception transducer array Rwx. A number of reception transducers in the reception transducer array Rwx is beneficially equal to or greater than a number of transducers included in the transmission aperture Tx. Further, the number of reception transducers may be a total number of the transducers 110a of the probe 110. According to the present embodiment, the number of reception transducers is the number of transmission transducers.

The input unit 1411 generates a sequence of RF signals obtained by the reception transducer array Rw corresponding to a transmission event and stores generated RF signals for each transmission event in the RF signal storage 1412. According to the present embodiment, the RF signal storage 1412 is configured to use the internal semiconductor memory of the FPGA 1 of the reception beamformer 140. However, the RF signal storage 1412 may be outside the FPGA 1. FIG. 6B is a schematic diagram illustrating correspondence between RF signal sequences in the transmitter 141 and addresses of the RF signal storage 1412. The RF signal storage 1412 is a memory that holds a generated RF signal until delay-and-sum processing is performed in order to generate an acoustic line signal. As illustrated in FIG. 6B, the RF signal storage 1412 is partitioned in a transducer array direction (azimuth direction) into a number of addresses equal to the number of input channels and in a subject depth direction into a number of addresses $D_{PART}$ (where $D_{PART}$ is a natural number). According to the present embodiment, when considering a maximum delay of a reflected wave in delay-and-sum processing, $D_{PART}$ is set from 2,000 to 8,000 words, for example, and is smaller than a number of partitions for holding RF signals corresponding to a target region Bx in the subject depth direction (corresponding to about 16,000 to 20,000 words). RF signals are generated in the order in which reflected ultrasound is obtained and are stored in order with a signal at a shallow position of the subject first, such that the RF signal storage 1412 functions as a first in, first out (FIFO) memory.

(2) Delay-and-Sum Unit 142

The delay-and-sum unit 142 is a circuit that, corresponding to a transmission event, (i) sets the target region Bx representing a position in the subject for which acoustic line signal line data is generated, and (ii) when an index corresponding to azimuth direction coordinates is i and an index corresponding to depth direction coordinates is j, for each of a plurality of observation points Pij (i=1 to N, j=1 to D) in the target region Bx, performs delay-and-sum calculations in a range of a reception aperture Rx for RF signal sequences received by reception transducers Rw from the observation point Pij, and (iii) generates acoustic line signal line data ds(q) (where q=1 to $q_{max}$; $q_{max}$ is the number of lines of acoustic line signal line data; in the first reception beamforming processing $q_{max}$=ML, and in the second reception beamforming processing $q_{max}$=NL) by calculating acoustic line signals dsij for each observation point Pij. As illustrated in FIG. 4, the delay-and-sum unit 142 includes a frame memory 1420, a focus controller 1421, a delay calculator 1422, a gain controller 1423, a memory controller 1424, a summing circuit 1425, a coordinate converter 1426, a filter 1427, a frame memory controller 1428, and an output unit 1429.

The following describes elements of the delay-and-sum unit 142 i) Focus Controller 1421

The focus controller 1421 sets the target region Bx for which acoustic line signal line data is generated in the subject. The "target region" is a region in the subject of signals for which acoustic line signal line data generation occurs in correspondence with a transmission event, and acoustic line signals dsij are generated with respect to observation points Pij in the target region Bx. The target region Bx is set as a set of target observation points for which acoustic line signal generation is performed, for convenience of calculation corresponding to one transmission event.

Here, "acoustic line signal line data" is defined as a data set from a set of acoustic line signals dsij with respect to all observation points Pij in the target region Bx generated from one transmission event, classified into delay-and-sum results (acoustic line signals dsij) with respect to observation points on lines, such that delay-and-sum results (acoustic line signals dsij) for one line are combined into one sequence. Acoustic line signal line data from different transmission events acquired at different times synthesized with reference to position of an observation point Pij is referred to as acoustic line signal frame data.

The focus controller 1421 sets the target region Bx, corresponding to a transmission event, based on information indicating position of the transmission aperture Tx acquired from the transmission beamformer 130.

Figure 7:
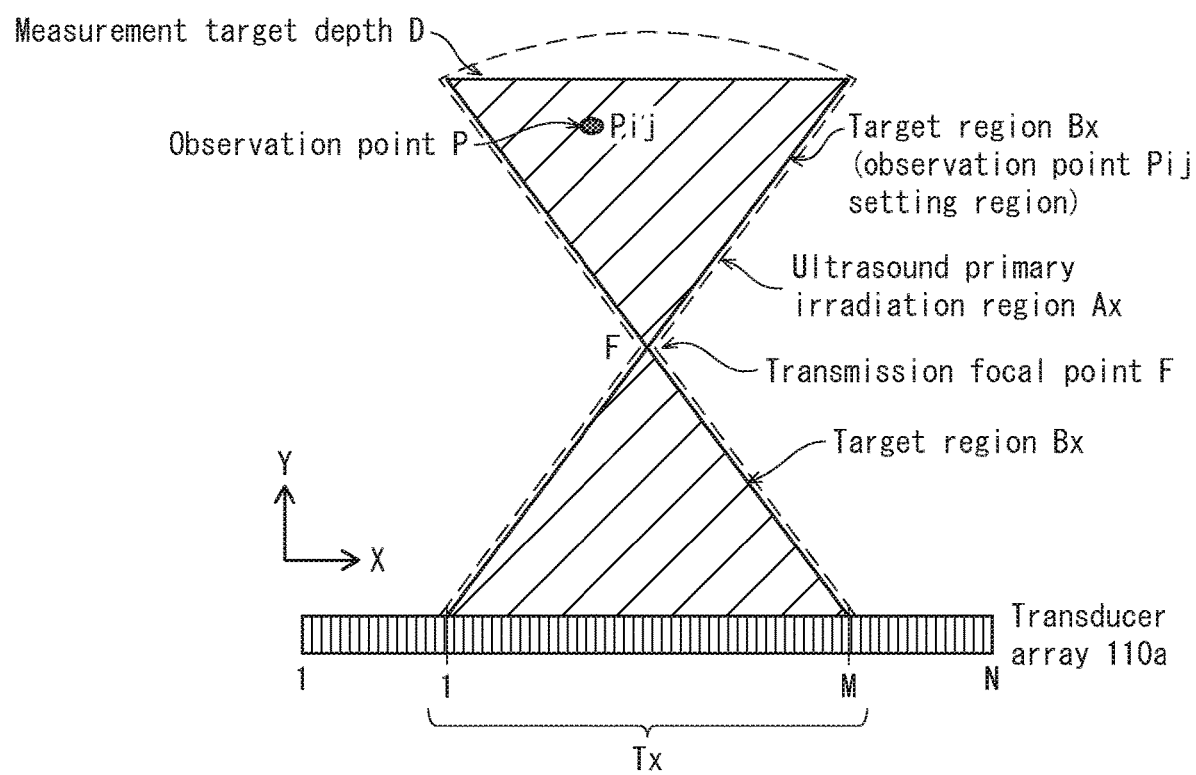
FIG. 7 is a schematic diagram illustrating a maximum range of a target region Bx that can be set in a first reception beamforming processing.

FIG. 7 is a schematic diagram illustrating a maximum range of a target region Bx that can be set in first reception beamforming processing. As illustrated in FIG. 7, the target region Bx exists in the ultrasound primary irradiation region Ax. The target region Bx is, in the ultrasound primary irradiation region Ax, an entire region for which depth is equal or less than the focal depth and a region for which depth is greater than the focal depth up to a measurement target depth D designated by a user via the controller 180. Further, a central axis of the target region Bx matches a central axis of the ultrasound primary irradiation region. Note that the target region Bx may be only a portion of the ultrasound primary irradiation region Ax.

The following is a description of positions of observation points Pij in the target region Bx in the first reception beamforming processing and the second reception beamforming processing.

FIG. 8A is a schematic diagram illustrating an example of positions of observation points Pij for acquiring acoustic line signals with respect to the transmission aperture Tx, in order to generate acoustic line signal line data ds(q) in the first reception beamforming processing. In the first reception beamforming processing, q (q=1 to ML; in FIG. 8A, ML=5) virtual lines may be set, passing through a transmission focal point F, and on each virtual line a finite number of observation points Pij may be set for generation of acoustic line signals. Here, a set of acoustic line signals obtained with respect to observation points Pij on the same virtual line is acoustic line signal line data ds(q) (q=1 to ML).

FIG. 8B and FIG. 8C are schematic diagrams illustrating examples of positions of observation points Pij for acquiring acoustic line signals with respect to the transmission aperture Tx, in order to generate acoustic line signal line data ds(q) in the second reception beamforming processing. In the second reception beamforming processing, q (q=1 to NL; in FIG. 8B, NL=1; in FIG. 8C, NL=3) virtual lines normal to the azimuth direction may be set, and on each virtual line a finite number of observation points Pij may be set for generation of acoustic line signals. Here, a set of acoustic line signals obtained with respect to observation points Pij on the same virtual line is set as acoustic line signal line data ds(q) (q=1 to NL).

Positions of observation points Pij set in the target region Bx are output to the delay calculator 1422.

Further, the focus controller 1421 selects reception transducers (reception transducer array) as a portion of the transducers of the probe 110 in order to set the reception aperture Rx, based on information indicating position of the transmission aperture Tx from the transmission beamformer 130.

Figure 9:
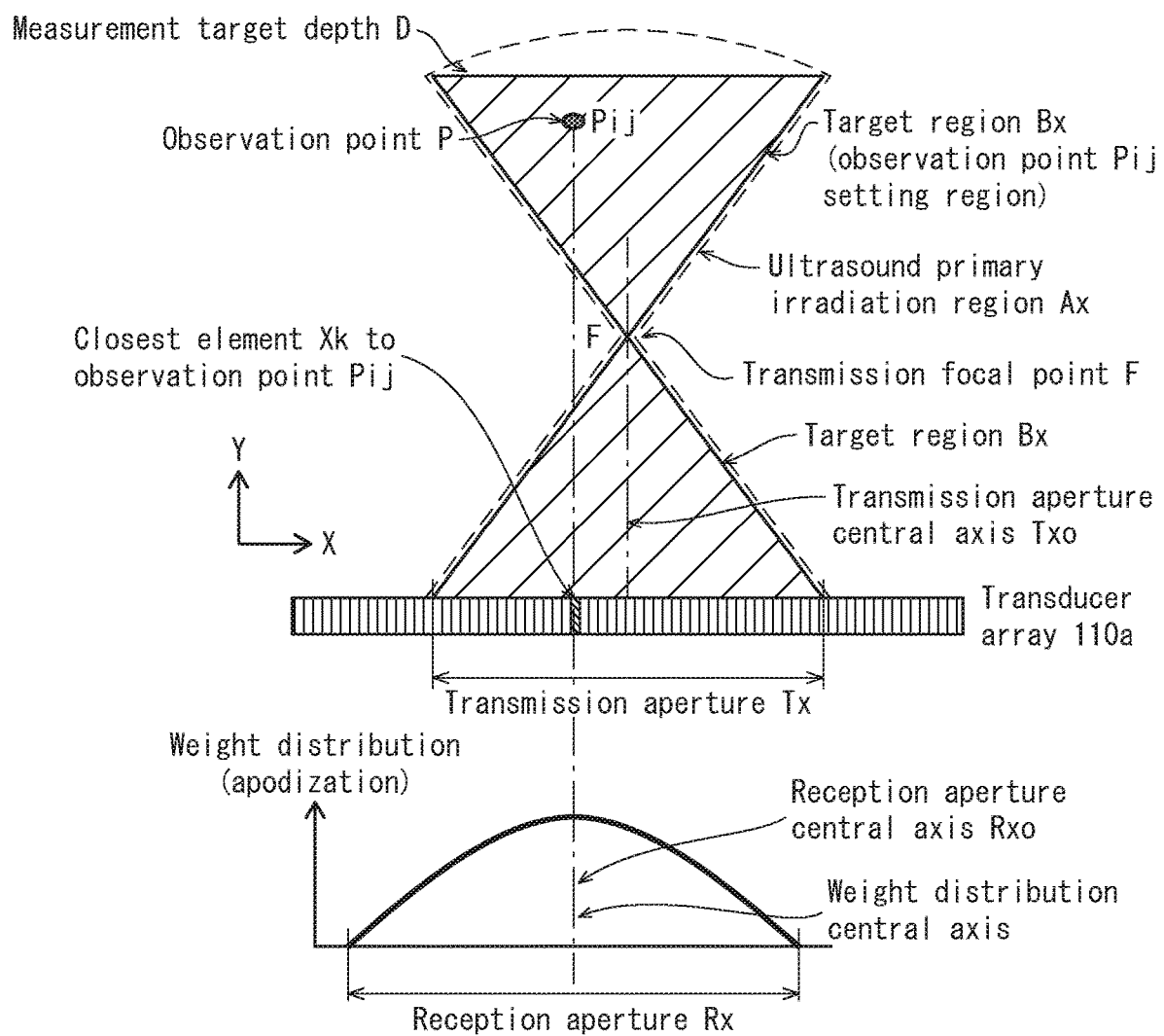
FIG. 9 is a schematic diagram illustrating a positional relationship between a reception aperture Rx and an observation point Pij.

Here, the focus controller 1421 selects the reception aperture Rx transducer array such that an array center thereof coincides with a transducer Xk that is spatially closest to an observation point Pij. FIG. 9 is a schematic diagram illustrating a positional relationship between the reception aperture Rx set by the focus controller 1421 and an observation point Pij. As illustrated in FIG. 9, the reception aperture Rx transducer array is selected such that the array center of the reception aperture Rx transducer array coincides with the transducer Xk that is spatially closest to the observation point Pij. Therefore, even in different transmission events, when generating acoustic line signals for a given observation point Pij in the same position, delay-and-sum is performed based on RF signals obtained by the same reception transducers Rk in the same reception aperture Rx. The selection method of the reception aperture Rx transducer array is the same for the first reception beamforming processing and the second reception beamforming processing.

Further, a number of transducers included in the reception aperture Rx for receiving reflected ultrasound from the ultrasound primary irradiation region is beneficially set to be at least the number of transducers included in the transmission aperture Tx of the corresponding transmission event. Setting of the reception aperture Rx is performed at least a number of times equal to a maximum number of observation points Pij in the array direction.

Information indicating position of the selected reception aperture Rx is outputted to the delay calculator 1422.

ii) Delay Calculator 1422

The delay calculator 1422 calculates transmission time for transmitted ultrasound to reach an observation point P in the subject. On the basis of information indicating the position of transducers included in the transmission aperture Tx acquired from the controller 180 and information indicating position of the target region Bx acquired from the focus controller 1421, the delay calculator 1422 calculates time taken for a transmitted ultrasound wave to arrive at an observation point Pij in a subject, for each observation point Pij in the target region Bx.

Figure 10A:
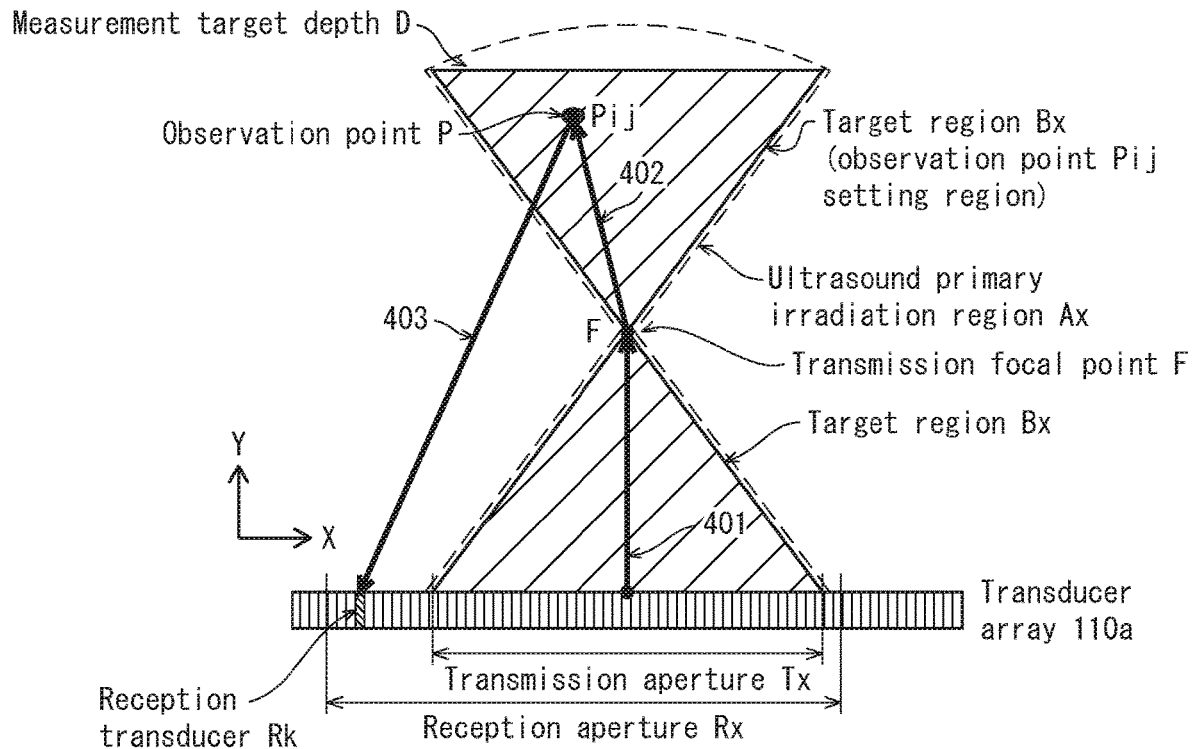
FIG. 10A and FIG. 10B are schematic diagrams illustrating propagation paths of ultrasound arriving at reception transducer Rk from transmission aperture Tx via observation point Pij.
Figure 10B:
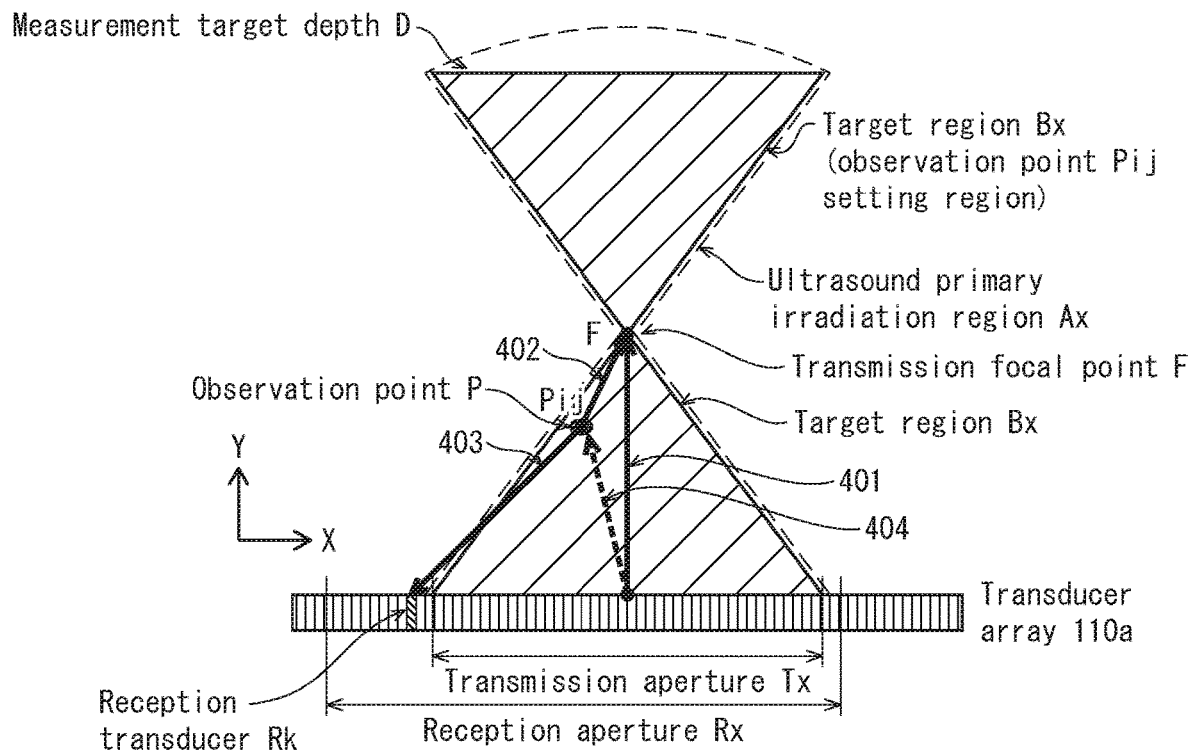

FIG. 10A and FIG. 10B are schematic diagrams illustrating propagation paths of ultrasound arriving at a reception transducer Rk in the reception aperture Rx, reflected from an observation point Pij at a position in the target region Bx and emitted from the transmission aperture Tx. FIG. 10A illustrates a case in which an observation point Pij is deeper than the focal depth, and FIG. 10B illustrates a case in which depth of an observation point Pij is less than the focal depth.

A wavefront of a transmitted wave emitted from the transmission aperture Tx converges at the transmission focal point F via a path 401 then diffuses. A transmitted wave arrives at an observation point Pij while converging or diffusing, and if there is a change in acoustic impedance at the observation point Pij a reflected wave is generated, the reflected wave returning to a reception transducer Rk in the reception aperture Rx of the probe 110. The transmission focal point F is defined as a control parameter of the transmission beamformer 130, and therefore length of a path 402 between the transmission focal point F and any observation point Pij can be geometrically calculated.

A method of calculating transmission time is described in more detail below.

First, as illustrated in FIG. 10A, when an observation point Pij is deeper than the focal depth, transmission time is calculated assuming that ultrasound emitted from the transmission aperture Tx arrives at the transmission focal point F via the path 401, then arrives at the observation point Pij via the path 402 from the transmission focal point F. Accordingly, a value obtained by summing a travel time along the path 401 and a travel time along the path 402 is the transmission time of a transmission wave. More specifically, for example, a total path length obtained by summing length of the path 401 and length of the path 402 can be divided by propagation speed of ultrasound in a subject in order to obtain the transmission time.

On the other hand, as illustrated in FIG. 10B, when an observation point Pij is shallower than or at an equal depth to the focal depth, transmission time is calculated assuming that, for ultrasound emitted from the transmission aperture Tx, time to arrive at the transmission focal point F via the path 401 and time to arrive at the transmission focal point F from the observation point Pij via a path 404 and the path 402 are equal. In other words, a value obtained by subtracting a travel time of a transmission wave along the path 402 from a travel time along the path 401 becomes the transmission time. More specifically, for example, a path length difference obtained by subtracting length of the path 402 from length of the path 401 can be divided by propagation speed of ultrasound in a subject in order to obtain the transmission time.

The delay calculator 1422 calculates the transmission times for ultrasound to arrive at each observation point Pij in the target region Bx in a subject for one transmission event.

Further, the delay calculator 1422 is a circuit that calculates reception time for reflected waves to arrive at each of the reception transducers Rk included in the reception aperture Rx from an observation point P. On the basis of information indicating the positions of reception transducers Rk acquired from the focus controller 1421 and information indicating position of the target region Bx, the delay calculator 1422 calculates reception time taken for a transmitted ultrasound wave reflected at each observation point Pij in a subject to arrive at each reception transducer Rk of the reception aperture Rx.

As described above, a transmission wave arriving at an observation point Pij generates a reflected wave at the observation point Pij, and the reflected wave returns to reception transducers Rk in the reception aperture Rx of the probe 110, and length of a path 403 from any observation point Pij to each reception transducer Rk can be geometrically calculated.

The delay calculator 1422 calculates, for every observation point Pij in the target region Bx for one transmission event, the reception times for transmitted ultrasound reflected at an observation point Pij to arrive at each reception transducer Rk.

Further, the delay calculator 1422 calculates total propagation time to each reception transducer Rk in the reception aperture Rx from transmission times and reception times, then based on the total propagation times, calculates delay to apply to RF signal sequences corresponding to the reception transducers Rk. The delay calculator 1422 acquires transmission times for ultrasound transmitted from the transducers 110a to arrive at observation points Pij and reception times for ultrasound reflected at the observation points Pij to arrive at each reception transducer Rk. The delay calculator 1422 then calculates total propagation times for transmitted ultrasound to arrive at reception transducers Rk and calculates delay for each of the reception transducers Rk based on differences in total propagation times of the reception transducers Rk. The delay calculator 1422 calculates, for all observation points Pij in the target region Bx, delay to apply to RF signal sequences corresponding to each reception transducer Rk.

The total propagation time calculation method may be the same for the first reception beamforming processing and the second reception beamforming processing. Alternatively, in the second reception beamforming processing, transmission time may be calculated based on straight line distance from the transmission aperture Tx to observation point Pij, and reception time may be calculated based on straight line distance from the observation point Pij to each reception transducer Rk, in order to simply calculate total propagation time.

iii) Memory Controller 1424

The memory controller 1424 identifies, among RF signal sequences corresponding to reception transducers Rk of the reception aperture Rx, RF signals corresponding to delays with respect to reception transducers Rk as RF signals corresponding to reception transducers Rk, based on ultrasound reflected from observation points Pij. More specifically, corresponding to a transmission event, the memory controller 1424 receives as input from the focus controller 1421 information indicating positions of reception transducers Rk, information indicating position of the target region Bx, and delays applied to RF signals for each reception transducer Rk. From RF signal sequences corresponding to reception transducers Rk acquired from the RF signal storage 1412, the memory controller 1424 identifies RF signals corresponding to times from which delays of reception transducers Rk are subtracted as RF signals based on reflected waves from observation points Pij, and outputs to the summing circuit 1425.

iv) Gain Controller 1423

The gain controller 1423 is a circuit that calculates a weighting sequence (reception apodization) with respect to each reception transducer Rk such that a weight of a transducer positioned at a center of the reception aperture Rx in the array direction is a maximum weight.

Figure 11:
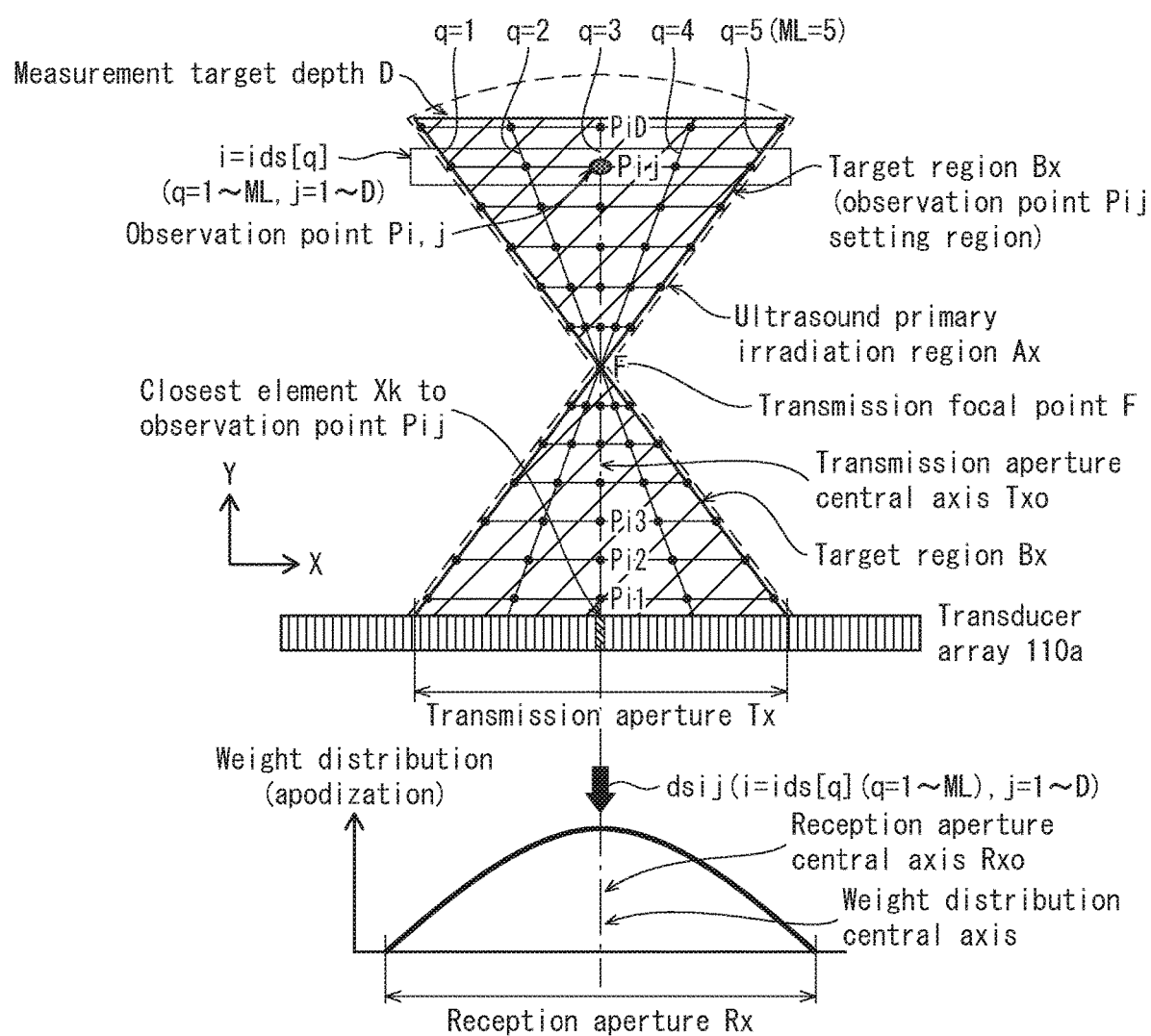
FIG. 11 is a schematic diagram illustrating a relationship between position of observation points Pij for acquiring an acoustic line signal to generate line data ds(q) and an array ids[q] of azimuth direction coordinates of observation points Pij in the first reception beamforming processing.

As illustrated in FIG. 11, the weighting sequence is a sequence of weighting coefficients applied to RF signals corresponding to each transducer in the reception aperture Rx. The weighting sequence has a symmetric distribution with the transmission focal point F as a center. As a shape of a weighting sequence distribution, a Hamming window, a Hann window, a rectangular window, or the like can be used, and the shape of distribution is not limited to any particular example. The weighting sequence is set so that weight for the transducer positioned at the center of the reception aperture Rx is a maximum, and a central axis of weight distribution coincides with a reception aperture central axis Rxo. The gain controller 1423 receives as input information indicating positions of reception transducers Rk outputted from the focus controller 1421, calculates a weighting sequence for each reception transducer Rk, and outputs to the summing circuit 1425.

v) Summing Circuit 1425

The summing circuit 1425 receives RF signals identified as corresponding to reception transducers Rk outputted from the memory controller 1424, sums the RF signals, and generates delay-and-sum processed acoustic line signals with respect to observation points Pij. Alternatively, the summing circuit 1424 may be configured to receive the weighting sequence with respect to each reception transducer Rk outputted from the gain controller 1423, multiply RF signals identified as corresponding to reception transducers Rk by weights corresponding to the reception transducers Rk, and generate acoustic line signals with respect to observation points Pij. Based on output of the delay calculator 1422, the memory controller 1424 arranges phases of RF signals detected by reception transducers Rk positioned in the reception aperture Rx so that the summing circuit 1425 performs summing processing, thereby superimposing RF signals received by reception transducers Rk based on reflected ultrasound from the observation points Pij, thereby increasing signal-to-noise ratio and enabling extraction of RF signals from observation points Pij. The summing processing method is the same for the first reception beamforming processing and the second reception beamforming processing.

The summing circuit 1425 generates a set of acoustic line signals dsij for all observation points Pij in the target region Bx in correspondence with a transmission event, i.e., acoustic line signal line data ds(q).

Figure 12:
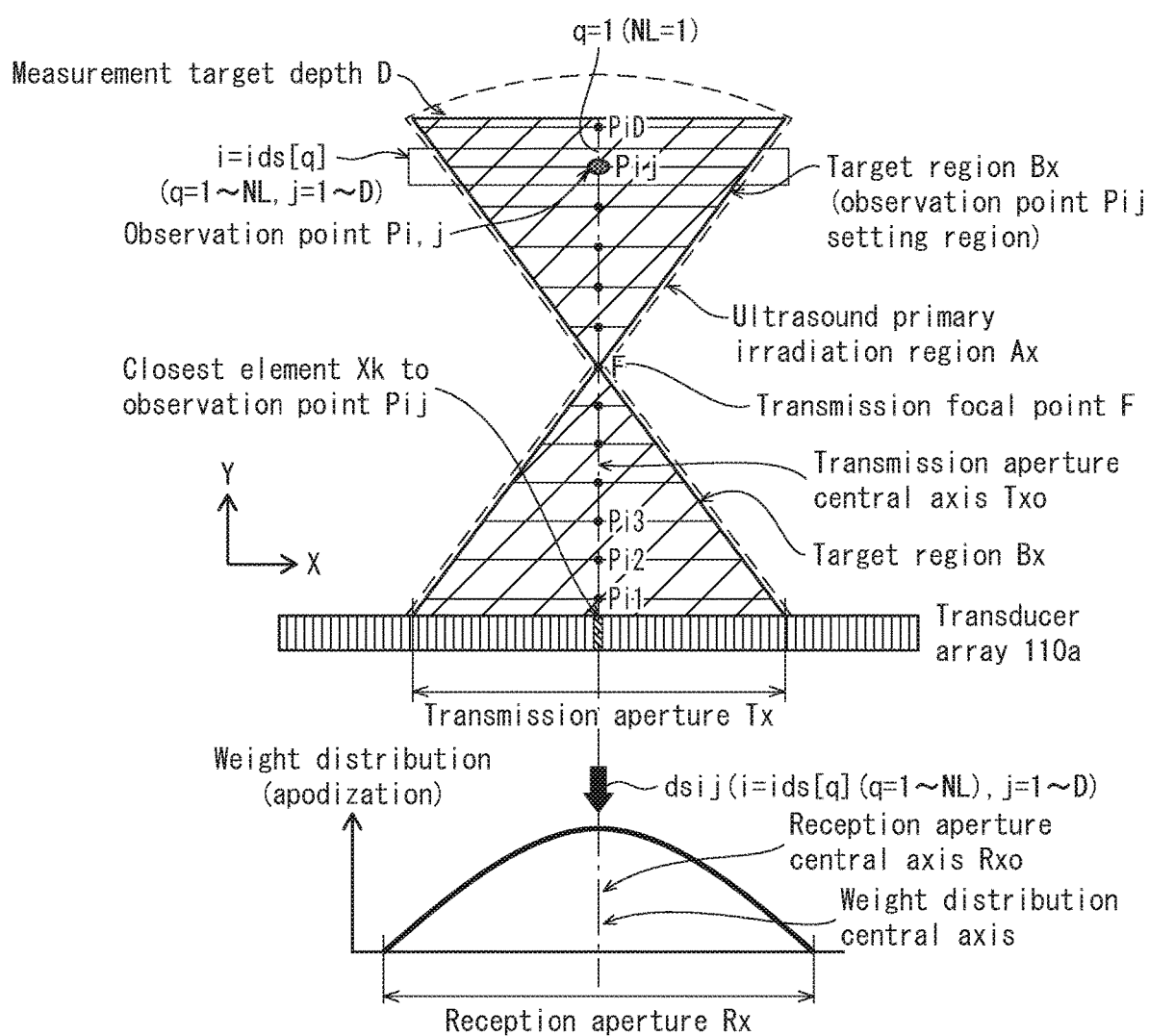
FIG. 12 is a schematic diagram illustrating a relationship between position of observation points Pij for acquiring an acoustic line signal to generate line data ds(q) and an array ids[q] of azimuth direction coordinates of observation points Pij in the second reception beamforming processing.

FIG. 11 is a schematic diagram illustrating a relationship between position of observation points Pij for acquiring acoustic line signals to generate acoustic line signal line data ds(q) and an array ids[q] of azimuth direction coordinates of observation points Pij, in the first reception beamforming processing. FIG. 12 is a schematic diagram illustrating a relationship between position of observation points Pij for acquiring acoustic line signals to generate acoustic line signal line data ds(q) and an array ids[q] of azimuth direction coordinates of observation points Pij, in the second reception beamforming processing. As illustrated in FIG. 11 and FIG. 12, the acoustic line signal line data ds(q) (where q is an index identifying acoustic line signal line data and q=1 to ML or NL) can be expressed as acoustic line signal dsij (where i=ids[q]; j=1 to D) by using the array ids[q] of azimuth direction coordinates of observation points Pij.

Generated acoustic line signal line data ds(q) is outputted to the frame memory 1420 for each transmission event, and additional processing is performed subsequently.

Further, ultrasound transmission is repeated while shifting the transmission aperture Tx in the array direction by a movement pitch Mp corresponding to transmission events, and by performing ultrasound transmission from all N of the transducers 110a of the probe 110 acoustic line signal frame data is generated, which is one frame of synthesized acoustic line signals.

vi) Filter 1427

The filter 1427 is a circuit that up-samples acoustic line signals, and the second reception beamforming processing may be configured to output generated acoustic line signals via the filter 1427. A high pass filter such as a finite impulse response (FIR) filter can be used. However, the filter 1427 is not limited to this. For examples, a least square filter, a polynomial approximation filter, an eigenvector filter, or the like may be used.

According to the present embodiment, the filter 1427 outputs acoustic line signals to the frame memory controller 1428, and the frame memory controller 1428 outputs the acoustic line signals as is to the output unit 1429.

vii) Coordinate Converter 1426

The coordinate converter 1426, the frame memory controller 1428, and the frame memory 1420 (also referred to collectively as a synthesizer) are circuitry that generates acoustic line signal frame data from acoustic line signal line data generated for a transmission event in the first reception beamforming processing. That is, the synthesizer sums acoustic line signal line data based on positions of observation points Pij for which acoustic line signals included in the acoustic line signal line data are acquired, thereby summing acoustic line signals for each observation point to generate acoustic line signal frame data. Thus, acoustic line signals are summed for an observation point at a given position.

Figure 13A:
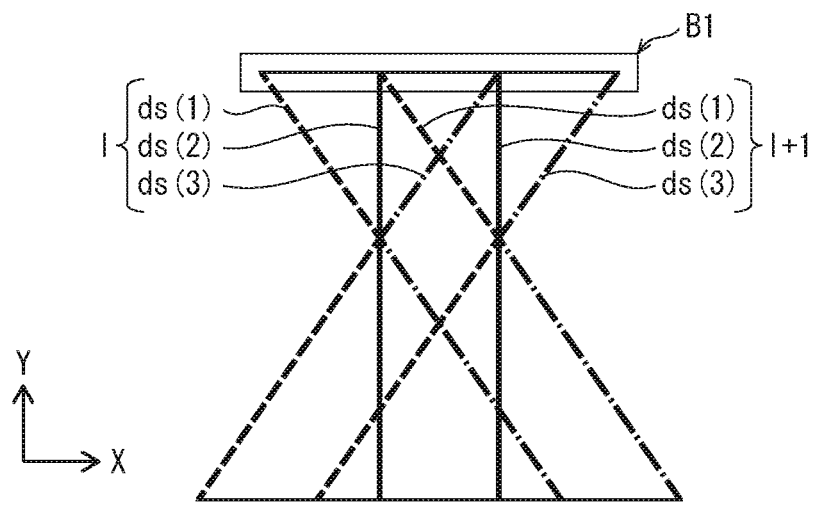
FIG. 13A is a schematic diagram illustrating a positional relationship of coordinates at which acoustic line signal line data dsij is acquired in sequential transmission events 1 and 1+1 in the first reception beamforming processing.
Figure 13B:
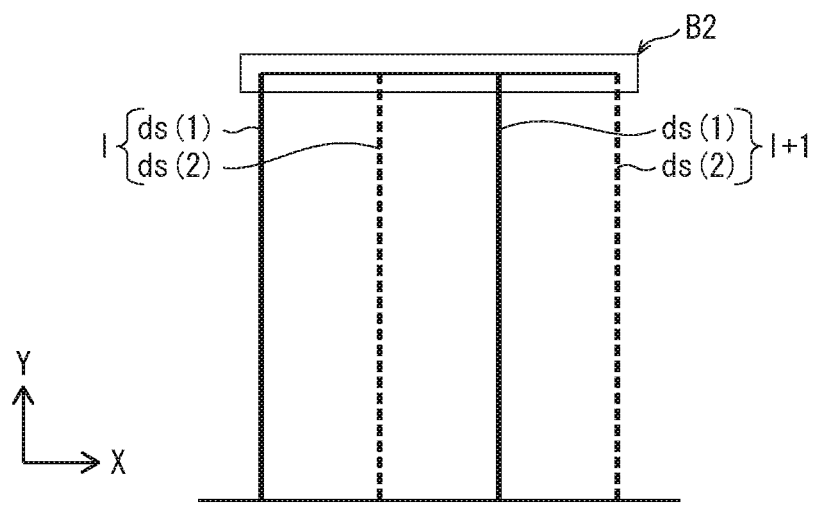
FIG. 13B is a schematic diagram illustrating a positional relationship of coordinates at which acoustic line signal line data dsij is acquired in sequential transmission events 1 and 1+1 in the second reception beamforming processing.

FIG. 13A is a schematic diagram illustrating a positional relationship of coordinates at which acoustic line signal line data dsij is acquired in sequential transmission events 1 and 1+1 in the first reception beamforming processing, and FIG. 13B is a schematic diagram illustrating a positional relationship of coordinates at which acoustic line signal line data dsij is acquired in sequential transmission events 1 and 1+1 in the second reception beamforming processing.

The coordinate converter 1426 assigns coordinate information of observation points Pij for which acoustic line signals are acquired, with respect to acoustic line signals in each acoustic line signal line data ds(q) (q=1 to ML or NL) generated corresponding to a transmission event. More specifically, the coordinate converter 1426 outputs to the frame memory controller 1428 acoustic line signals of acoustic line signal line data ds(q) (q=1 to ML or NL; in FIG. 13A, ML=3; in FIG. 13B, ML=2) and coordinate information of observation points Pij for which the acoustic line signals are acquired.

viii) Frame Memory 1420

The frame memory 1420 is a semiconductor memory. Acoustic line signal line data ds(q) acquired by different transmission events is summed at addresses corresponding to positions of observation points Pij, thereby synthesizing synthesized acoustic line signals with respect to each observation point. According to the present embodiment, the frame memory 1420 is configured to use the internal semiconductor memory of the FPGA of the reception beamformer 140, like the RF signal storage 1412. The frame memory 1420 is partitioned in a transducer array direction (azimuth direction) into a number of addresses equal to the number of input channels and in a subject depth direction into a number of addresses D (where D is a natural number). According to the present embodiment, the transducer array direction (azimuth direction) is partitioned into 96 or 192 addresses and D is partitioned into 4000 to 12000 addresses, for example.

ix) Frame Memory Controller 1428, Output Unit 1429

The frame memory controller 1428 designates addresses of the frame memory 1420 corresponding to observation point Pij coordinate information, sums an acoustic line signal with data held at the designated address, and replaces the data held at the designated address with a result of the summing.

Thus, an acoustic line signal generated corresponding to a transmission event can be synthesized based on position of an observation point Pij from which the acoustic line signal is acquired.

The output unit 1429 is a circuit that outputs acoustic line signals generated at the delay-and-sum unit 142 to the main summing unit 143.

As described above, in the first reception beamforming processing, in chronological order of transmission events, the frame memory controller 1428 performs processing of acquiring acoustic line signal line data from the coordinate converter 1426, designating an address of the frame memory 1420 to output an acoustic line signal, and summing with data stored in the frame memory 1420. Further, the frame memory controller 1428 controls output of acoustic line signals with respect to the frame memory 1420 based on instruction from the controller 180, and the output unit 1429 outputs acoustic line signals output from the frame memory 1420 to the main summing unit 143.

Figure 14A:
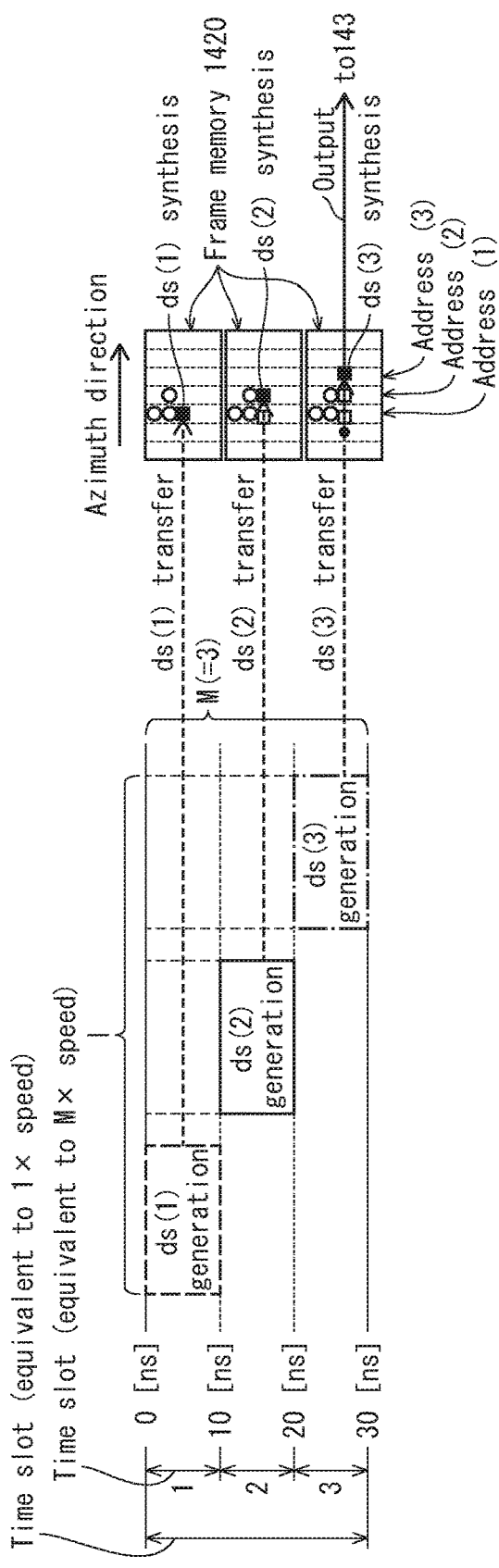
FIG. 14A and FIG. 14B are schematic diagrams illustrating generation of acoustic line signal line data ds(q) and timing of output from frame memory in sequential transmission events 1 and 1+1 in the first reception beamforming processing.
Figure 14B:
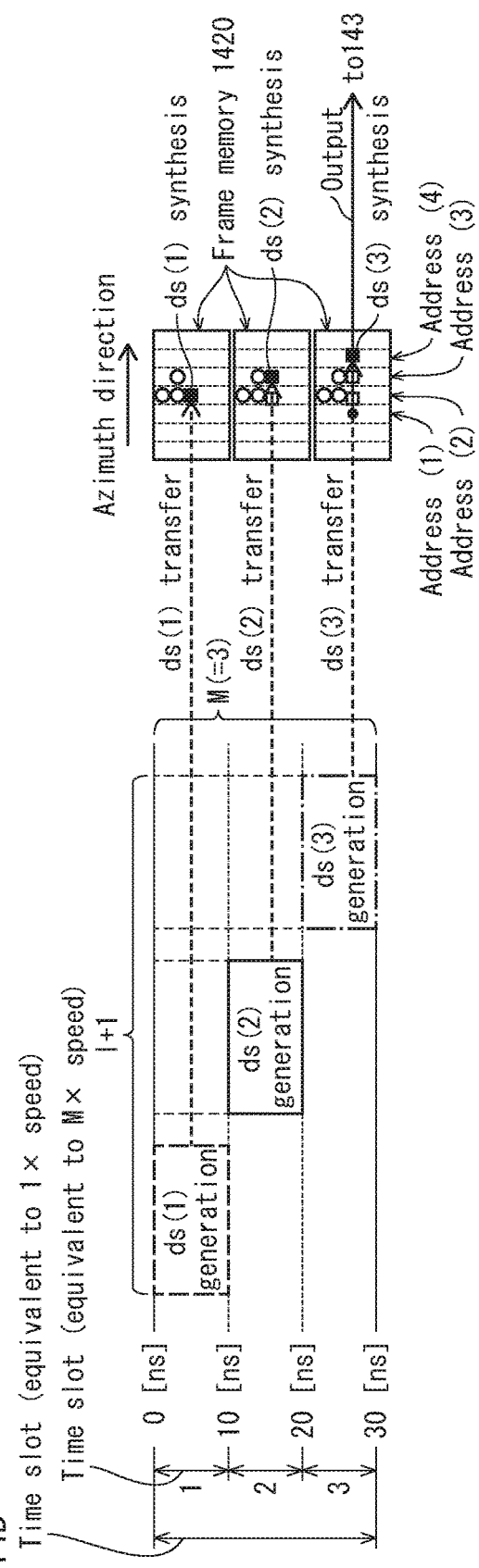

FIG. 14A and FIG. 14B are schematic diagrams illustrating generation of acoustic line signal line data ds(q) and timing of output from the frame memory 1420 in sequential transmission events 1 and 1+1 in the first reception beamforming processing illustrated in FIG. 13A. In FIG. 14A and FIG. 14B, a portion of the frame memory 1420 is illustrated corresponding to addresses corresponding to coordinates of portion B1 in FIG. 13A.

Figure 15A:
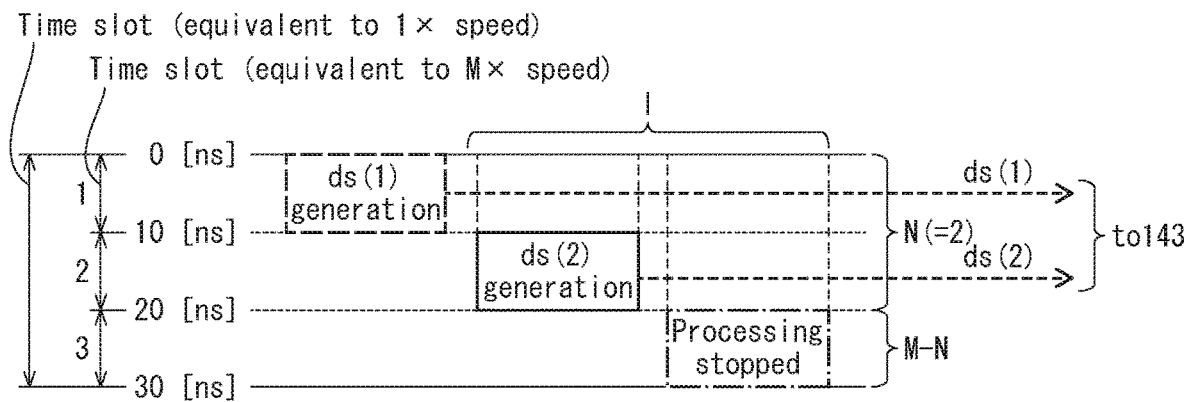
FIG. 15A and FIG. 15B are schematic diagrams illustrating generation of acoustic line signal line data ds(q) and timing of output from frame memory in sequential transmission events 1 and 1+1 in the second reception beamforming processing.
Figure 15B:
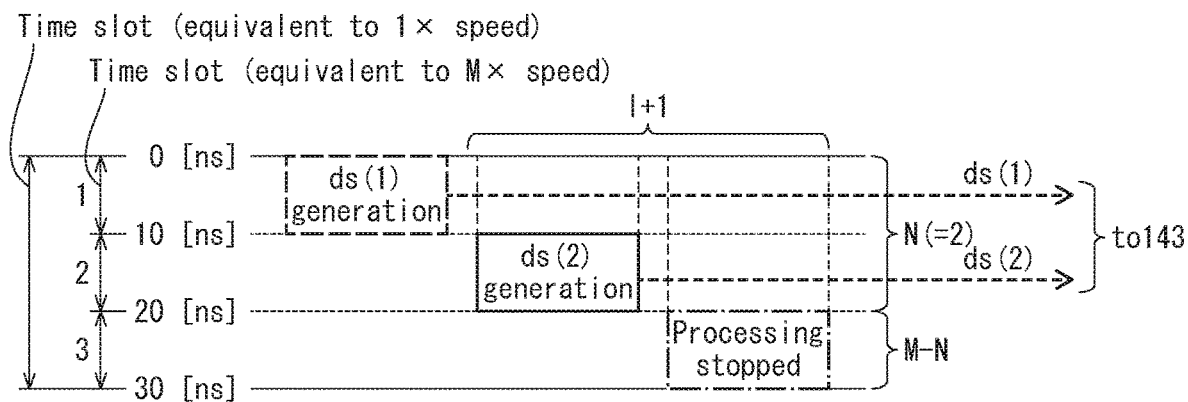

Further, FIG. 15A and FIG. 15B are schematic diagrams illustrating generation of acoustic line signal line data ds(q) and timing of output from the frame memory 1420 in sequential transmission events 1 and 1+1 in the second reception beamforming processing illustrated in FIG. 13B.

In the delay-and-sum unit 142, in the first reception beamforming processing, first, as illustrated in FIG. 14A, in transmission event 1, the frame memory controller 1428 specifies an address of the frame memory 1420 corresponding to information of coordinates of an observation point Pij for which acoustic line signal line data ds(1), ds(2), ds(3) is acquired, sums an acoustic line signal with data held at the address, and overwrites the data held at the address with a result of summing.

First, in transmission event 1, summing results of past transmission events 1−1, 1−2 have been written to addresses (1), (2) in the frame memory 1420 (indicated by white circles "○" in the drawings). In this state, as illustrated in FIG. 14A, acquisition positions of acoustic line signals of portion B1 are ds(1), ds(2), ds(3) in order in a positive direction along the X axis. Thus, as illustrated in FIG. 14A, acoustic line signals ds(1), ds(2), ds(3) (indicated by black squares "■" in the drawings) are summed with data (indicated by white circles "0" in the drawings) held at corresponding addresses S (addresses (1), (2), (3)) in the frame memory 1420, and summing results overwrite data at the corresponding addresses S. Then, the frame memory controller 1428 outputs to the main summing unit 143, via the output unit 1429, an acoustic line signal (indicated by a black circle "●" in the drawings) at address (1) after summing of the acoustic line signal generated in past transmission event 1−2, the acoustic line signal generated in past transmission event 1−1, and the acoustic line signal generated in the present transmission event 1 is complete.

Next, in transmission event 1+1, summing results of past transmission events 1, 1−1 have been written to addresses (2), (3) in the frame memory 1420 (indicated by white circles "0" in the drawings). In this state, as illustrated in FIG. 14B, acoustic line signals ds(1), ds(2), ds(3) (indicated by black squares "■" in the drawings) are summed with data (indicated by white circles "○" in the drawings) held at corresponding addresses S (addresses (2), (3), (4)) in the frame memory 1420, and summing results overwrite data at the corresponding addresses S. Then, the frame memory controller 1428 outputs to the main summing unit 143, via the output unit 1429, an acoustic line signal (indicated by a black circle "●" in the drawings) at address (2) after summing of the acoustic line signal generated in past transmission event 1−1, the acoustic line signal generated in past transmission event 1, and the acoustic line signal generated in the present transmission event 1+1 is complete.

Further, generation of the acoustic line signal line data ds(1), ds(2), ds(3) in the delay-and-sum unit 142 and summing with data in the corresponding address S in the frame memory 1420 is performed in one time slot, which is one sample period divided by the number ML (in FIG. 14A and FIG. 14B, ML=3) of acoustic line signal line data to be obtained, which in this example is 10 ns. The acoustic line signal line data ds(1), ds(2), ds(3) are time division processed into three time slots in one transmission event.

More specifically, as illustrated in FIG. 14A and FIG. 14B, in the transmission event 1 or l+1, in a time slot 1, the acoustic line signal line data ds(1) is summed and written to the address (1) (or address (2) in transmission event l+1). Further, in time slot 2, the acoustic line signal line data ds(2) is summed and written to the address (2) (or address (3) in transmission event l+1). Further, in time slot 3, the acoustic line signal line data ds(3) is summed and written to the address (3) (or address (4) in transmission event l+1), and at the same time, acoustic line signal line data at the address (1) (or address (2) in transmission event l+1) marked with a black circle "●" is read and output for subsequent processing.

By using this configuration, simultaneous access to the frame memory 1420 does not occur with respect to summing processing related to acoustic line signal line data ds(1), ds(2), ds(3), and therefore 1-read/1-write (1R1 W) type single port static random access memory (SRAM) can be used, and hardware cost of the frame memory 1420 can be further reduced. Further, for example, a mounting area can be further reduced when compared to a case in which the frame memory 1420 comprises a multiport memory such as a 2R1 W type, a 2R2 W type, or the like.

Further, in the second reception beamforming processing, first, as illustrated in FIG. 14B, in transmission event 1, the frame memory controller 1428 does not store acoustic line signal line data ds(1), ds(2) in the frame memory 1420, and outputs in the order generated, chronologically, to the main summing unit 143 via the output unit 1429.

Here, generation of (NI, lines of) acoustic line signal line data ds(1), ds(2) in the delay-and-sum unit 142 and output to the main summing unit 143 is performed in two time slots selected from the three 10 ns time slots derived from dividing one sample period by the number ML (in FIG. 14A and FIG. 14B, ML=3) of acoustic line signal line data to be obtained in the first reception beamforming processing. In the remaining one (ML−NL) time slot, processing is stopped. That is, the NL lines of acoustic line signal line data ds(1), ds(2) are not processed in two time slots obtained by dividing one sample period by the number NL (in FIG. 15A and FIG. 15B, NL=2) of lines of acoustic line signal line data to be obtained in one sample period, and are instead chronologically processed in two time slots selected from three time slots derived from dividing the one sample period by the number ML.

More specifically, as illustrated in FIG. 15A and FIG. 15B, in the transmission event 1 or l+1, in the time slot 1, the acoustic line signal line data ds(1) is generated and outputted to the main summing unit 143. In the time slot 2, the acoustic line signal line data ds(2) is generated and outputted. In the time slot 3, processed is stopped.

By adopting such a configuration, it is possible to generate acoustic line signal line data within the same time slots in both the first reception beamforming processing and the second reception beamforming processing. Thus, transfer rates between circuit modules can be equalized or closely approximated between the first reception beamforming processing and the second reception beamforming processing. Here, "closely approximated" indicates that a difference between ML and NL is in a range of about ±15 lines.

Further, by performing summing processing of acoustic line signal line data in the delay-and-sum unit 142 in the first reception beamforming processing, the number of lines of acoustic line signal line data transferred to the main summing unit 143 from the delay-and-sum unit 142 can be reduced when compared to a case where acoustic line signal line data summing processing is performed in the main summing unit 143. Thus, an increase in the interface specification between the delay-and-sum unit 142 and the main summing unit 143, which are circuit modules in the reception beamformer 140, and an increases in required specification of the main summing unit 143, which is a subsequent stage circuit module, can be suppressed, and hardware cost of the reception beamformer 140 can be reduced.

(3) Main Summing Unit 143

The main summing unit 143 is a circuit that arranges acoustic line signal line data generated in the delay-and-sum units 142 corresponding to a transmission event based on coordinates of observation points Pij from which the data is acquired, in order to generate acoustic line signal frame data.

FIG. 5 is a function block diagram illustrating configuration of the main summing unit 143 of the FPGA 2. As illustrated in FIG. 5, the main summing unit 143 includes input units 1431_1, 1431_2 that input acoustic line signal line data outputted from the output units 1429 of the delay-and-sum units 142_1, 142_2, a summing circuit 1432 that generates acoustic line signal frame data arranged with reference to coordinates of observation points Pij for which acoustic line signal line data is acquired, and a transmission circuit 1433 that performs direct memory access (DMA) transfer of the acoustic line signal frame data to the ultrasound image generator 150. The summing circuit 1432 generates acoustic line signal frame data by arranging acoustic line signal line data for all transmission events. Generated acoustic line signal frame data is transmitted to the ultrasound image generator 150 from the transmission circuit 1433 for each transmission event or each set of transmission events.

Figure 16:
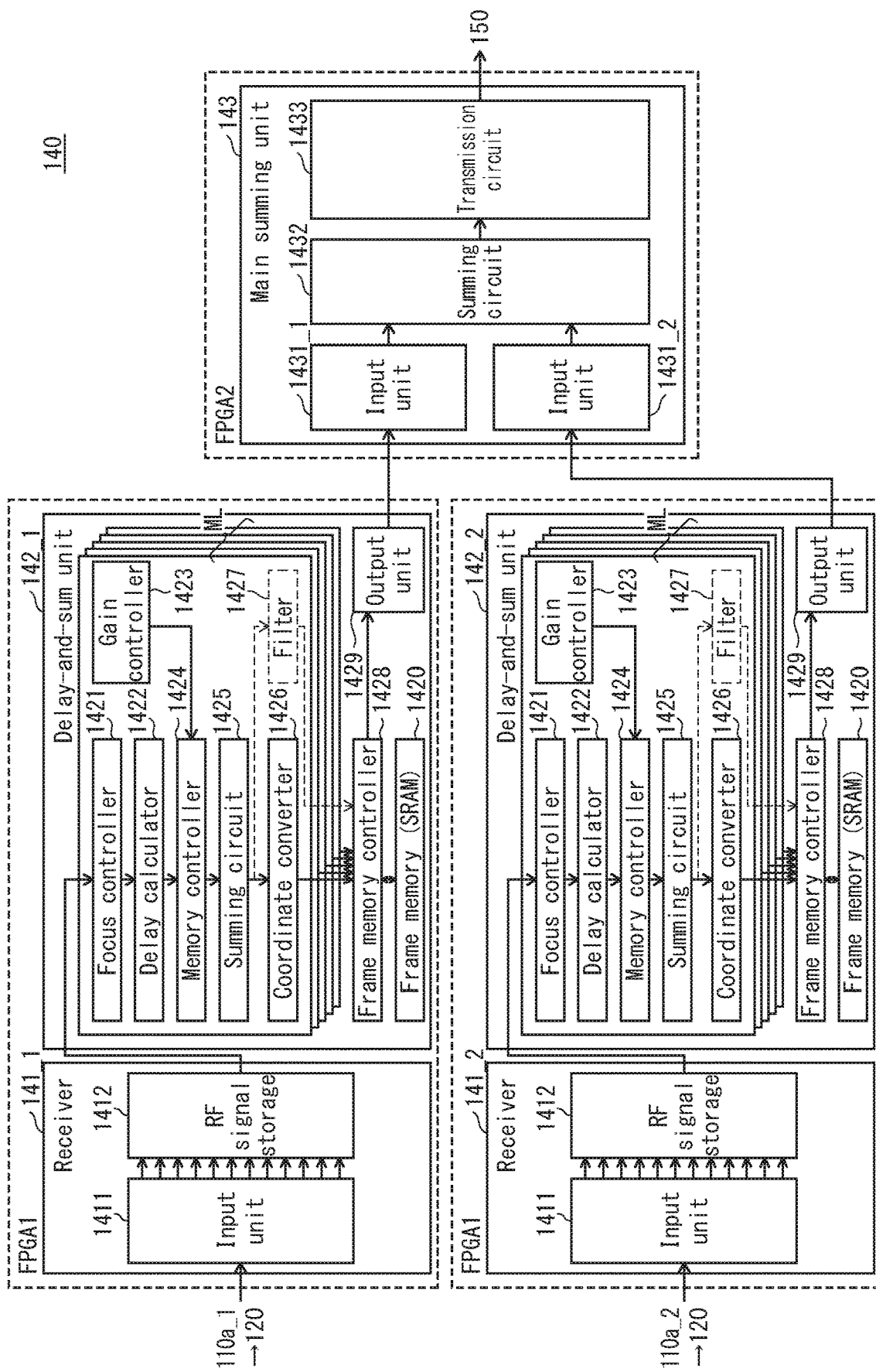
FIG. 16 is a function block diagram illustrating a reception beamformer 140 in the first reception beamforming processing.
Figure 17:
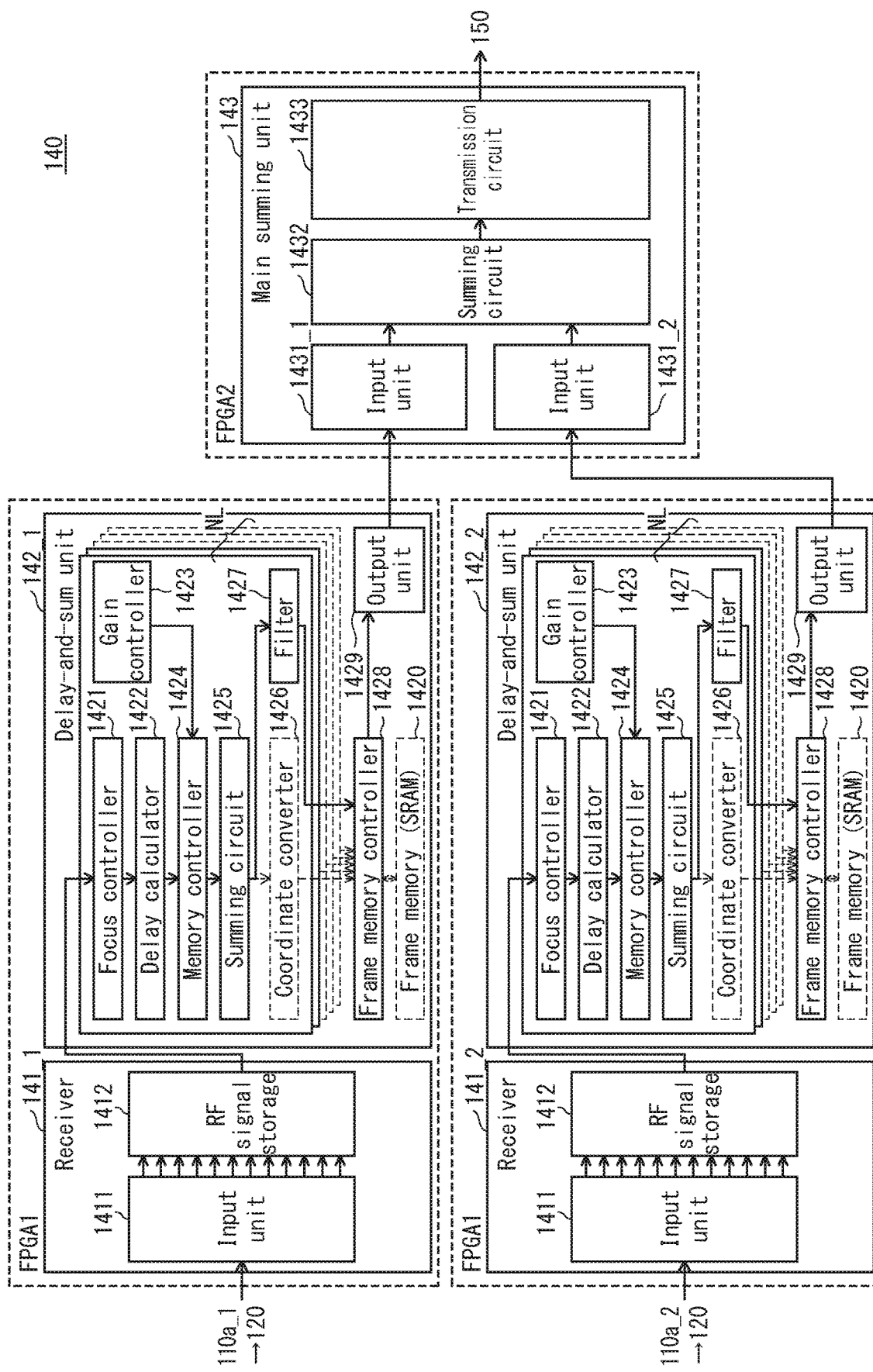
FIG. 17 is a function block diagram illustrating the reception beamformer 140 in the second reception beamforming processing.

(4) Circuit Block Operation in First and Second Reception Beamforming Processing The reception beamformer 140 includes functions of the first reception beamforming processing according to a synthetic aperture method and the second reception beamforming processing according to a simple delay-and-sum method, and selectively executes beamforming processing based on various operation conditions in ultrasound measurement. As illustrated in FIG. 4, the delay-and-sum unit 142 includes the frame memory 1420, the focus controller 1421, the delay calculator 1422, the gain controller 1423, the memory controller 1424, the summing circuit 1425, the coordinate converter 1426, the filter 1427, the frame memory controller 1428, and the output unit 1429. Of these, elements of the delay-and-sum unit 142 that operate in the first reception beamforming processing and the second reception beamforming processing are different. FIG. 16 is a function block diagram illustrating the reception beamformer 140 in the first reception beamforming processing. FIG. 17 is a function block diagram illustrating the reception beamformer 140 in the second reception beamforming processing. In FIG. 16 and FIG. 17, circuit blocks indicated by solid lines function, and operation of circuit blocks indicated by broken lines is stopped. More specifically, in the first reception beamforming processing, the frame memory controller 1428 sums ML lines of acoustic line signal line data generated in processing from the focus controller 1421 to the summing circuit 1425 with data held at addresses S in the frame memory 1420, and outputs acoustic line signals at addresses for which summing corresponding to the number of lines of acoustic line signal line data is complete to the main summing unit 143, via the output unit 1429.

On the other hand, in the second reception beamforming processing, the frame memory controller 1428, after upsampling by the filter 1427, outputs to the main summing unit 143, via the output unit 1429, NL lines of acoustic line signal line data generated in processing from the focus controller 1421 to the summing circuit 1425, in the order the data is generated, without storing the data in the frame memory 1420.

As described above, according to the ultrasound signal processing device 500 pertaining to the present embodiment, circuit size can be reduced when compared to reception beamforming circuitry that simply implements both delay-and-sum beamforming processing and synthetic aperture beamforming processing functions by using different circuit modules, by selectively causing operation of common circuit module elements when executing the first reception beamforming processing by a synthetic aperture method and when executing the second reception beamforming processing by a simple delay-and-sum method.

<Operations>

The following describes operations of the ultrasound diagnostic device 100 configured as described above.

Figure 18:
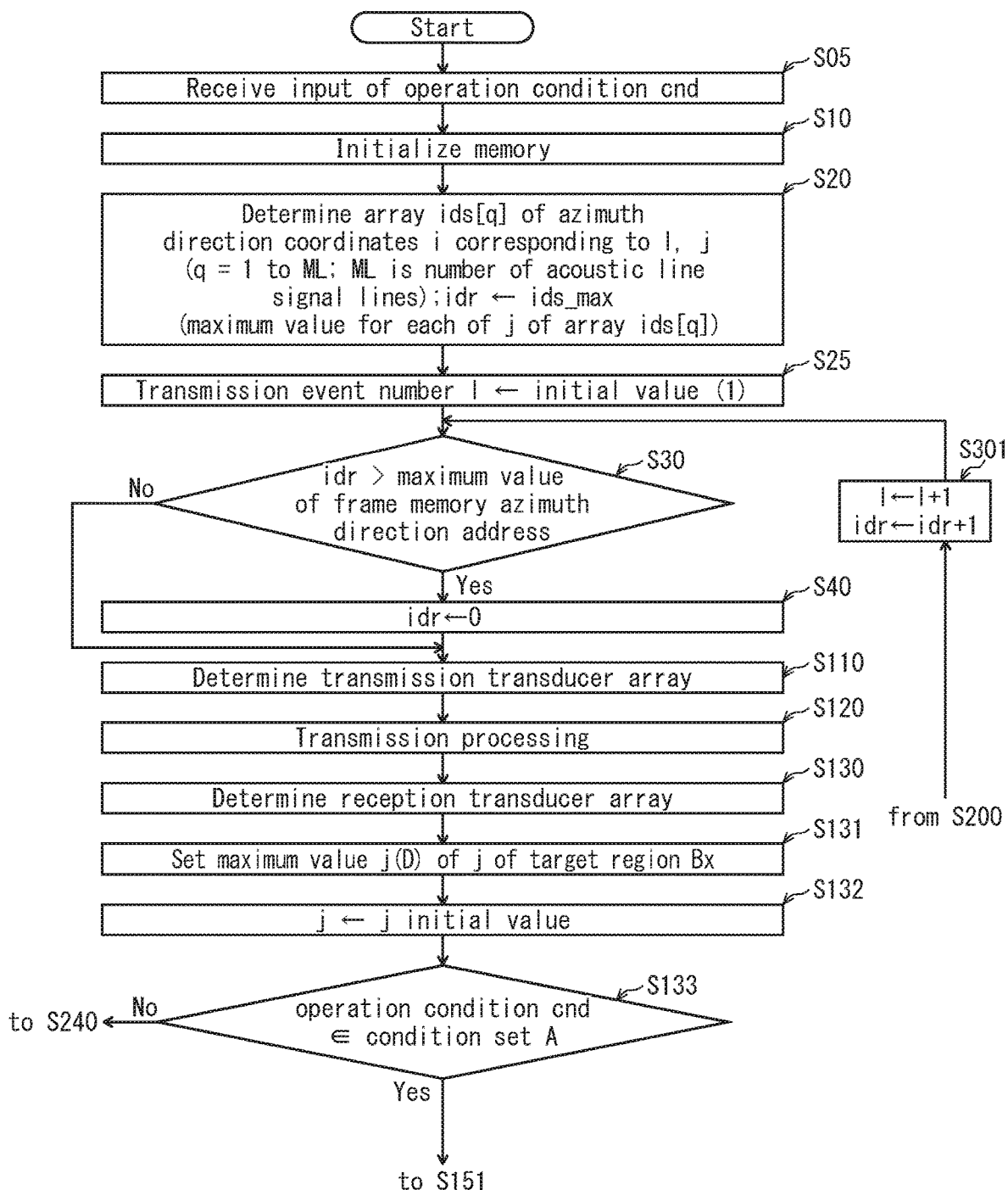
FIG. 18 is a flowchart illustrating beamforming processing of the reception beamformer 140 pertaining to Embodiment 1.
Figure 19:
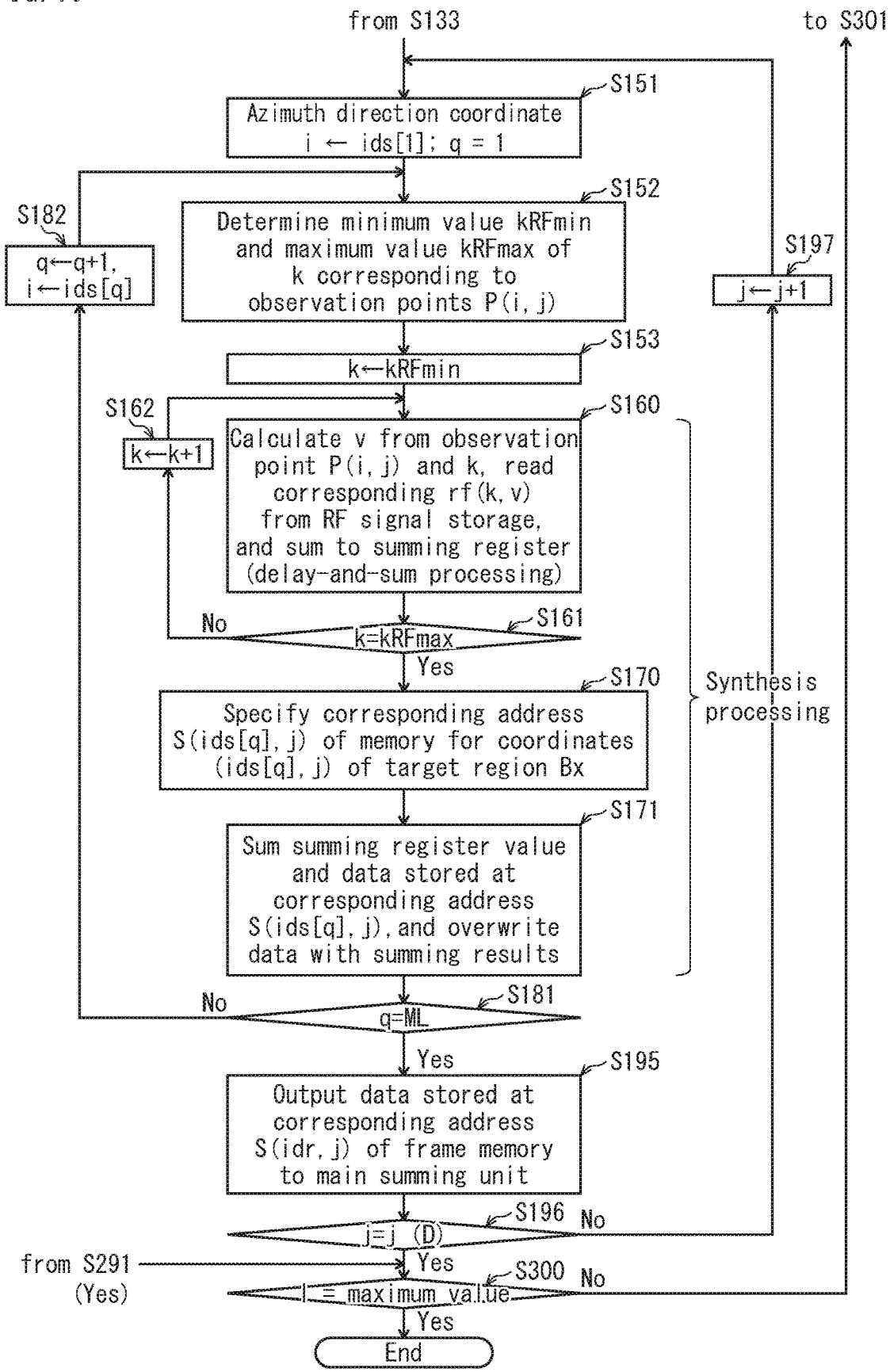
FIG. 19 is a flowchart illustrating beamforming processing of the reception beamformer 140 pertaining to Embodiment 1.
Figure 20:
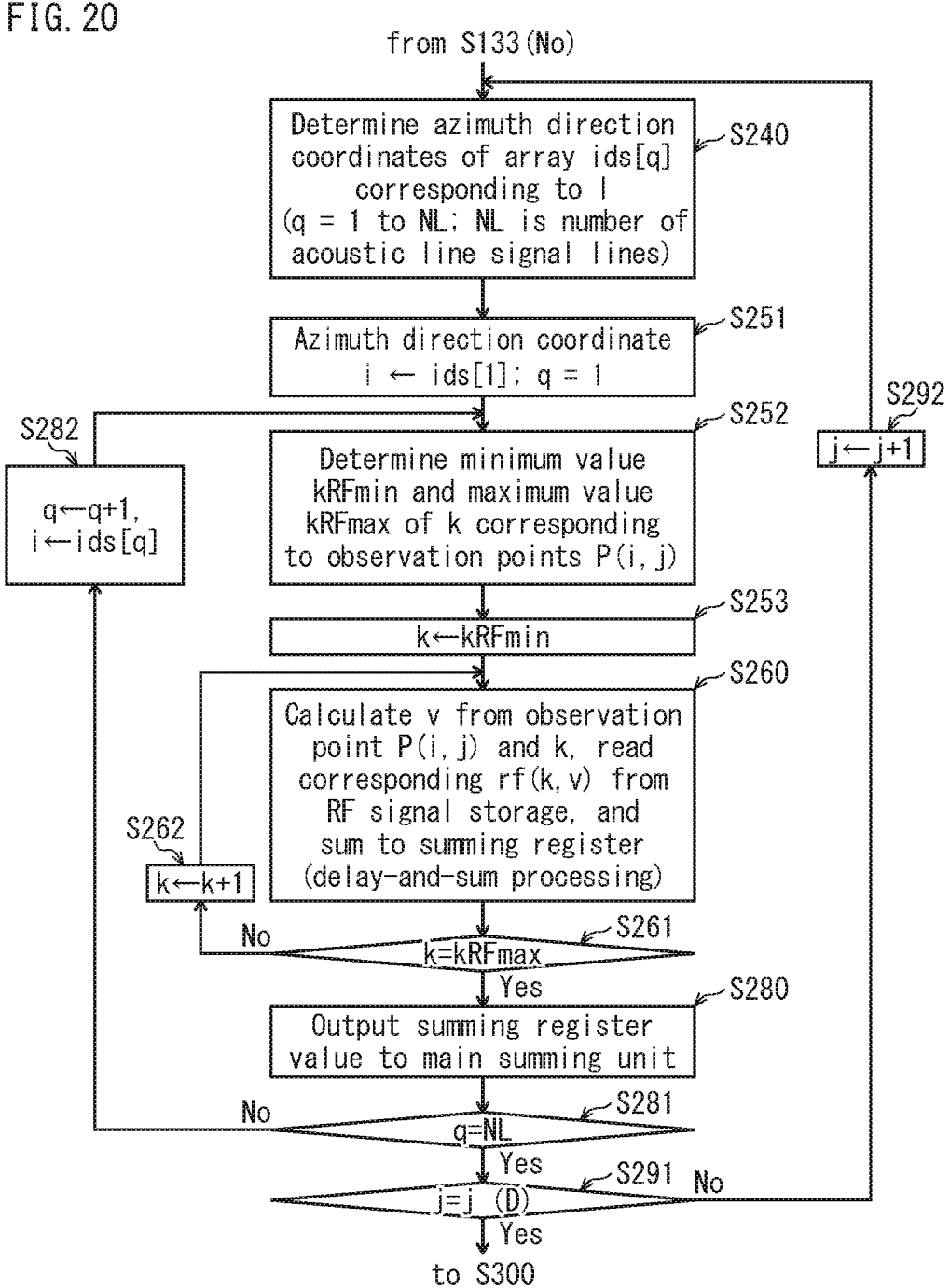
FIG. 20 is a flowchart illustrating beamforming processing of the reception beamformer 140 pertaining to Embodiment 1.

FIG. 18, FIG. 19, and FIG. 20 are flowcharts illustrating beamforming processing operations of the reception beamformer 140.

First, the controller 180 receives an operation condition cnd from an input unit (not illustrated) such as a keyboard, mouse, or the like (step S05). Operation conditions are ultrasound measurement operation conditions of the ultrasound diagnostic device 100, such as B mode selection, color Doppler mode selection, B mode and color Doppler mode combined mode selection, analysis target region (region of interest; ROI) selection, presence or absence of transmission steering, and the like.

Next, the RF signal storage 1412 and the frame memory 1420 are initialized, and data at all addresses are overwritten with zero values (step S10). Next, in the first reception beamforming processing by a synthetic aperture method, the focus controller 1421 determines an array ids[q] (where q=1 to ML; and ML is the number of lines of acoustic line signal line data generated in a transmission event) of azimuth direction coordinates of observation points Pij for which acoustic line signals are to be generated, corresponding to depth direction index j (step S20). As illustrated in FIG. 11, in the first reception beamforming processing, q virtual lines (where q=1 to ML; in FIG. 11, ML=5) passing through the transmission focal point F are set, and a finite number of observation points Pij are set on each virtual line. According to the present disclosure, a set of acoustic line signals obtained with respect to observation points Pij on the same virtual line is referred to as acoustic line signal line data.

Further, arrays ids[q] (where q=1 to ML; and ML is the number of lines of acoustic line signal line data generated in one transmission event) of azimuth direction coordinates i of observation points Pij for which acoustic line signals are generated corresponding to a depth direction index j are determined for all values of j, and a value idr is set to a maximum value ids[q]_max(idr) of the array ids[q] for all values of j (step S20).

Further, the value 1, indicating a transmission event number, is initialized to 1 (step S25).

Next, whether or not the value idr of the array ids[q] is larger than a maximum value of azimuth direction addresses of the frame memory 1420 is determined (step S30), if larger, the value idr is set to 0, and if not, processing proceeds to step S110.

Next, the transmitter 131 determines the transmission aperture Tx from the transducers 110a of the probe 110 (step S110), and performs transmission processing (a transmission event) supplying transmission signals for causing transmission of an ultrasound beam from transmission transducers included in the transmission aperture Tx (step S120).

Next, the receiver 141 determines the reception transducer array Rwx from the transducers 110a of the probe 110 (step S130).

Next, a maximum value j (D) is set for j in the target region Bx for which acoustic line signals are to be calculated (step S131) and j is set to an initial value (step S132).

Next, whether the operation condition cnd is included in a condition set A is determined (step S133). The condition set A is a set of operation conditions for performing the first reception beamforming processing by the synthetic aperture method. For example, the condition set A may be set such that various operation conditions in B mode are included in the condition set A and operations conditions in color Doppler mode, B mode and color Doppler mode combined mode, and transmission steering are not included in the condition set A. When the operation condition cnd is included in the condition set A, processing proceeds to step S151, and when not, processing proceeds to step S240.

Next, in FIG. 19, the index i indicating azimuth direction coordinates corresponding to j is set to an initial value ids[1] (q=1) (step S151).

Next, in step S152, a minimum value kRFmin and a maximum value kRFmax of an index k of the azimuth direction corresponding to observation points P(i,j) are determined, to set the reception aperture Rx, and k is set is to the minimum value kRFmin (step S153). Here, k is an index indicating position in the azimuth direction of transducers corresponding to RF signals referenced in delay-and-sum processing of observation points P(i,j).

Next, in step S160, the delay calculator 1422 calculates a value v corresponding to a delay amount, based on the observation point P(i,j) and k, the memory controller 1424 reads corresponding rf(k,v) from the RF signal holder 1412, and the summing circuit 1425 sums with a summing register (delay-and-sum processing). At this time, the gain controller 1423, as illustrated in FIG. 11, may multiply rf(k,v) by a weighting coefficient corresponding to k from the weighting distribution (apodization) centered on the central axis Rxo of the reception aperture Rx to perform summing.

Next, it is determined whether k is the maximum value kRFmax (step S161). If less than the maximum value, k is incremented (step S162) and processing returns to step S160. If k is equal to or greater than the maximum value, processing proceeds to step S170. By performing step S160 (delay-and-sum processing) for values of k in the azimuth direction corresponding to observation points P(i,j) from the minimum value kRFmin to the maximum value kRFmax, acoustic line signals (delay-and-sum (DAS) data) with respect to observation points P(i,j) are added to the summing register.

Next, in step S170, the coordinate converter 1426 specifies an address S (ids[q]j) of the frame memory 1420 corresponding to coordinates (ids[q]j) in the target region Bx. For example, the coordinate converter 1426 may set a sum of ids[q] and a value (1−1) obtained by subtracting 1 from the transmission event number 1 as an azimuth direction corresponding address S, and the address as a corresponding address S(ids[q],j), and outputs the corresponding address S(ids[q]j) to the frame memory controller 1428. The frame memory controller 1428 sums the summing register with the data held at the corresponding address S(ids[q],j), and overwrites the data with the summing result (step S171).

Next, it is determined whether or not q is the maximum value ML of acoustic line signals in the target region Bx (step S181). If less than the maximum value ML, q is incremented, i is set to a new ids[q] (step S182), and processing returns to step S152. When q is the maximum value ML in the target region Bx, an acoustic line signal ds(ids_maxj) for which synthesis processing in transmission events to this point is complete, held at the corresponding address (idr,j) of the frame memory 1420, is outputted to the main summing unit 143 (step S195).

In step S195, each acoustic line signal may be multiplied by amplification factors that are different in the depth direction and determined according to the number of times acoustic line signals are summed in the acoustic line signal ds(ids[q],j). At this stage, acoustic line signals ds(ids[q]j) of observation points P(i,j) corresponding to the array ids[q] (q=1 to ML) of all azimuth direction coordinates corresponding to the index j are generated, and are outputted to the frame memory 1420 for summing with data of corresponding addresses.

Next, whether or not j is the maximum value j(D) in the target region Bx is determined (step S196). If j is less than the maximum value j(D), j is incremented (step S197) and processing returns to step S151 to calculate an acoustic line signal ds(ids [q] j) for an observation point P(i,j) corresponding to a new array ids[q]. In this way, by incrementing j and repeating step S160, acoustic line signals ds(ids[q],j) are generated for observation points P(i,j) corresponding to the array ids[q] of all azimuth direction coordinates positioned in the target region Bx. If j is the maximum value j(D) in step S196, processing proceeds to step S319.

Next, whether all transmission events have been performed is determined depending on whether or not l, indicating the transmission event count, is a maximum value (step 300). If not completed, l and idr are incremented (step S301) and processing returns to step S30. A transmission event is executed, moving the transmission aperture Tx in the array direction by the movement pitch Mp, the coordinates (i,j) indicating position of an observation point P(i,j) are set with respect to the array ids[q] corresponding to j, based on a range of the target region Bx obtained from the transmission aperture Tx of the current transmission event, the minimum value kRFmin and the maximum value kRFmax for the observation point P(i,j) are determined (step S152), and acoustic line signal ds(ids[q] j) generation (delay-and-sum processing) is performed (step S160). If complete, the first reception beamforming processing according to the synthetic aperture method ends.

On the other hand, in the determination of whether or not the operation condition cnd is included in the condition set A in step S133, when it is determined that the operation condition cnd is not included in the condition set A, processing proceeds to step S240. In FIG. 20, in the second reception beamforming processing by the simple delay-and-sum method, first, the focus controller 1421 determines azimuth direction coordinates of the array ids[q] (where q=1 to NL; and NL is the number of lines of acoustic line signal line data generated in one transmission event) of observation points Pij for which acoustic line signals are to be generated corresponding to the index j in the depth direction (step S240).

As illustrated in FIG. 12, in the second reception beamforming processing, q virtual lines (where q=1 to NL; in FIG. 12, NL=1) normal to the azimuth direction, passing through the transmission focal point F, are set, and a finite number of observation points Pij are set on each virtual line.

Next, the index i indicating azimuth direction coordinates corresponding to j is set to an initial value ids[1] (q=1) (step S251).

Next, in step S252, a minimum value kRFmin and a maximum value kRFmax of the index k of the azimuth direction corresponding to observation points P(i,j) are determined, to set the reception aperture Rx, and k is set is to the minimum value kRFmin (step S253). Here, k is an index indicating position in the azimuth direction of transducers corresponding to RF signals referenced in delay-and-sum processing of observation points P(i,j).

Next, in step S260, the delay calculator 1422 calculates a value v corresponding to a delay amount, based on the observation point P(i,j) and k, the memory controller 1424 reads corresponding rf(k,v) from the RF signal holder 1412, and the summing circuit 1425 sums with a summing register (delay-and-sum processing). At this time, the gain controller 1423, as illustrated in FIG. 12, may multiply rf(k,v) by a weighting coefficient corresponding to k from the weighting distribution (apodization) centered on the central axis Rxo of the reception aperture Rx to perform summing.

Next, it is determined whether k is the maximum value kRFmax (step S261). If less than the maximum value, k is incremented (step S262) and processing returns to step S260. If k is equal to or greater than the maximum value, processing proceeds to step S280. By performing step S260 (delay-and-sum processing) for values of k in the azimuth direction corresponding to observation points P(i,j) from the minimum value kRFmin to the maximum value kRFmax, acoustic line signals (delay-and-sum (DAS) data) with respect to observation points P(i,j) are added to the summing register.

Next, in step S280, the frame memory controller 1428 outputs the summing register value to the main summing unit 134. At this time, the filter 1427 may perform upsampling processing and output a result to the main summing unit 134.

Next, it is determined whether or not q is the maximum value NL of acoustic line signals in the target region Bx (step S281). If less than the maximum value NL, q is incremented, i is set to a new ids[q] (step S282), and processing returns to step S252. If q is the maximum value NL in the target region Bx, acoustic line signals ds(ids[q],j) are generated for all observation points P(i,j) corresponding to an array ids[q] (q=1 to NL) of azimuth direction coordinates corresponding to the index j, and are outputted to the main summing unit 143.

Next, whether or not j is the maximum value j(D) in the target region Bx is determined (step S296). If j is less than the maximum value j(D), j is incremented (step S292) and processing returns to step S240 to calculate an acoustic line signal ds(ids[q],j) for an observation point P(i,j) corresponding to a new array ids[q] (step S160). In this way, by incrementing j and repeating step S260, acoustic line signals ds(ids[q],j) are generated for observation points P(i,j) corresponding to the array ids[q] of all azimuth direction coordinates positioned in the target region Bx. If j is the maximum value j(D) in step S291, processing proceeds to step S300.

Next, whether all transmission events have been performed is determined depending on whether or not 1, indicating the transmission event count, is a maximum value (step 300). If not completed, l and idr are incremented (step S301) and processing returns to step S30. A transmission event is executed, moving the transmission aperture Tx in the array direction by the movement pitch Mp, the coordinates (i,j) indicating position of an observation point P(i,j) are set with respect to the array ids[q] corresponding to j, based on a range of the target region Bx obtained from the transmission aperture Tx of the current transmission event (step S240), the minimum value kRFmin and the maximum value kRFmax for the observation point P(i,j) are determined (step S252), and acoustic line signal ds(ids[q]j) generation (delay-and-sum processing) is performed (step S260). If complete, the second reception beamforming processing according to the delay-and-sum method ends.

<Review>

The ultrasound signal processing device 500 pertaining to at least one embodiment is an ultrasound signal processing device comprising ultrasound signal processing circuitry, the ultrasound signal processing circuitry comprising the reception beamformer 140 that executes processing selected from first reception beamforming processing and second reception beamforming processing. The first reception beamforming processing includes generating, for each transmission event, a set of acoustic line signal line data including acoustic line signals associated with observation points where a portion of the observation points associated with one set have a same position as a portion of the observation points associated with another set, and synthesizing acoustic line signal line data by summing acoustic line signals that are associated with the observation points having same positions. The second reception beamforming processing includes generating, for each transmission event, a set of acoustic line signal line data including one or more acoustic line signals associated with the observation points, where positions of the observation points are different for each transmission event. Numbers of lines of the acoustic line signals generated per transmission event are different between the first reception beamforming processing and the second reception beamforming processing. The reception beamformer 140 includes the delay-and-sum unit 142 that performs delay-and-sum processing with respect to reception signal sequences from multiple channels based on reflected ultrasound to calculate the acoustic line signal line data. The delay-and-sum unit 142, in the first reception beamforming processing, synthesizes the acoustic line signal line data calculated in the delay-and-sum processing by summing the acoustic line signals associated with the observation points having the same positions, and in the second reception beamforming processing, outputs the acoustic line signal data calculated in the delay-and-sum processing as is. Time taken by the delay-and-sum unit 142 to generate the acoustic line signal line data per set of acoustic line signal line data is equal or approximately equal in the first reception beamforming processing and the second reception beamforming processing.

Conventionally, if the reception beamformer 140 were structured to simply implement both delay-and-sum beamforming processing and synthetic aperture beamforming processing, there is a technical problem that in a simple implementation transfer rates between circuit modules are made different, interface specifications between circuit modules in the reception beamforming circuit and required specifications of circuit modules in subsequent stages become high, and therefore hardware costs of the reception beamformer 140 would become high.

On the other hand, according to the ultrasound signal processing device 500 embodiment described above, transfer rates are equal or approximately equal between circuit modules in both the first reception beamforming processing and the second reception beamforming processing, and therefore an increase in interface specifications between the delay-and-sum unit 142 and the main summing unit 143, which are circuit modules in the reception beamformer 140, and an increase in required specifications of the main summing unit 143, which is a subsequent stage circuit module, can be suppressed, and hardware costs of the reception beamformer 140 can be reduced. As a result, it is possible to implement functions of both beamforming processing by a synthetic aperture method and beamforming processing by a simple delay-and-sum method in a simple structure in a reception beamforming circuit.

Further, the first reception beamforming processing and the second reception beamforming processing can be implemented by selective operation of components of a common circuit module, and in comparison to a structure in which both functions are simply implemented by different circuit modules, circuit scale of the reception beamformer 140 can be reduced.

According to at least one embodiment, the delay-and-sum unit 142 comprises the frame memory 1420, and in the first reception beamforming processing the delay-and-sum unit 142 performs the synthesis by summing the acoustic line signal line data with acoustic line signals associated with the observation points having the same positions previously written to addresses of the frame memory 1420 corresponding to the positions.

According to said structure, by performing summing processing of acoustic line signal line data in the delay-and-sum unit 142 in the first reception beamforming processing, the number of lines of acoustic line signal line data transferred to the main summing unit 143 from the delay-and-sum unit 142 can be reduced when compared to a case where acoustic line signal line data summing processing is performed in the main summing unit 143, and therefore an increase in interface specifications between the delay-and-sum unit 142 and the main summing unit 143, and an increase in required specifications of the main summing unit 143, which is a subsequent stage circuit module, can be suppressed. Further, an interface with a low transfer rate between the delay-and-sum unit 142 and the main summing unit 143 can be used, allowing more freedom in interface selection, and a low system cost can be realized.

According to at least one embodiment, the number of lines of the acoustic line signal line data outputted by the delay-and-sum unit 142 per transmission event is ML in the first reception beamforming processing, and NL in the second reception beamforming processing, and a maximum value of ML and NL is max(ML, NL), and the delay-and-sum unit 142, in processing generating and outputting max(ML, NL) lines of the acoustic line signal line data, generates and outputs the max(ML, NL) lines of the acoustic line signal line data in a max(ML, NL) cycle time slot period by operating at a max(ML, NL) multiple of processing speed.

According to said structure, it is possible to generate acoustic line signal line data within the same time slots in both the first reception beamforming processing and the second reception beamforming processing. Thus, an increase in the interface specification between the delay-and-sum unit 142 and the main summing unit 143, which are circuit modules in the reception beamformer 140, and an increase in required specification of the main summing unit 143, which is a subsequent stage circuit module, are suppressed, and hardware cost of the reception beamformer 140 can be reduced.

According to at least one embodiment, a minimum value of ML and NL is min(ML, NL), and the delay-and-sum unit 142, in processing generating and outputting min(ML, NL)

lines of the acoustic line signal line data, stops generation and output of the acoustic line signal line data in a (max(ML, NL)−min(ML, NL)) cycle time slot period.

According to said structure, by performing time-division processing (time slot processing) of max(ML,NL) double-speed operations, required circuit scale can be reduced, and system cost can be reduced. Further, time slot processing enables scalable processing and simplifies circuit structure.

According to at least one embodiment, the reception beamformer 140 comprises a plurality of the delay-and-sum unit 142, and the main summing unit 143 that further sums acoustic line signal line data outputted from the plurality of the delay-and-sum unit 142.

According to said structure, it is possible to configure a multi-channel reception beamforming circuit using a plurality of circuit modules including the delay-and-sum unit 142. Further, the main summing unit can be structured by only a simple summing circuit and a DMA transfer circuit, reducing system cost of the beamformer.

<Modification 1>

Although an ultrasound signal processing device pertaining to at least one embodiment has been described above, the present disclosure is not limited to the embodiment described above, except for essential characteristic elements thereof. For example, embodiments obtained by various modifications conceivable by a person skilled in the art applied to any described embodiment, and any combination of elements and functions of any embodiment that does not depart from the spirit of the present disclosure are included in the present disclosure. The following describes ultrasound signal processing devices pertaining to modifications as examples of such embodiments.

The following describes a configuration of an ultrasound signal processing device pertaining to Modification 1.

According to Embodiment 1, the reception beamformer 140 includes a plurality of the delay-and-sum unit 142, and the main summing unit 143 that further sums acoustic line signal line data outputted from the delay-and-sum units 142 and outputs to a subsequent stage. The delay-and-sum unit 142 includes the first frame memory 1420. In the first reception beamforming processing, for each transmission event, acoustic line signal line data is synthesized by summing acoustic line signal data for observation points at the same position written to an address in the first frame memory 1420 corresponding to the observation points at the same position.

Figure 21:
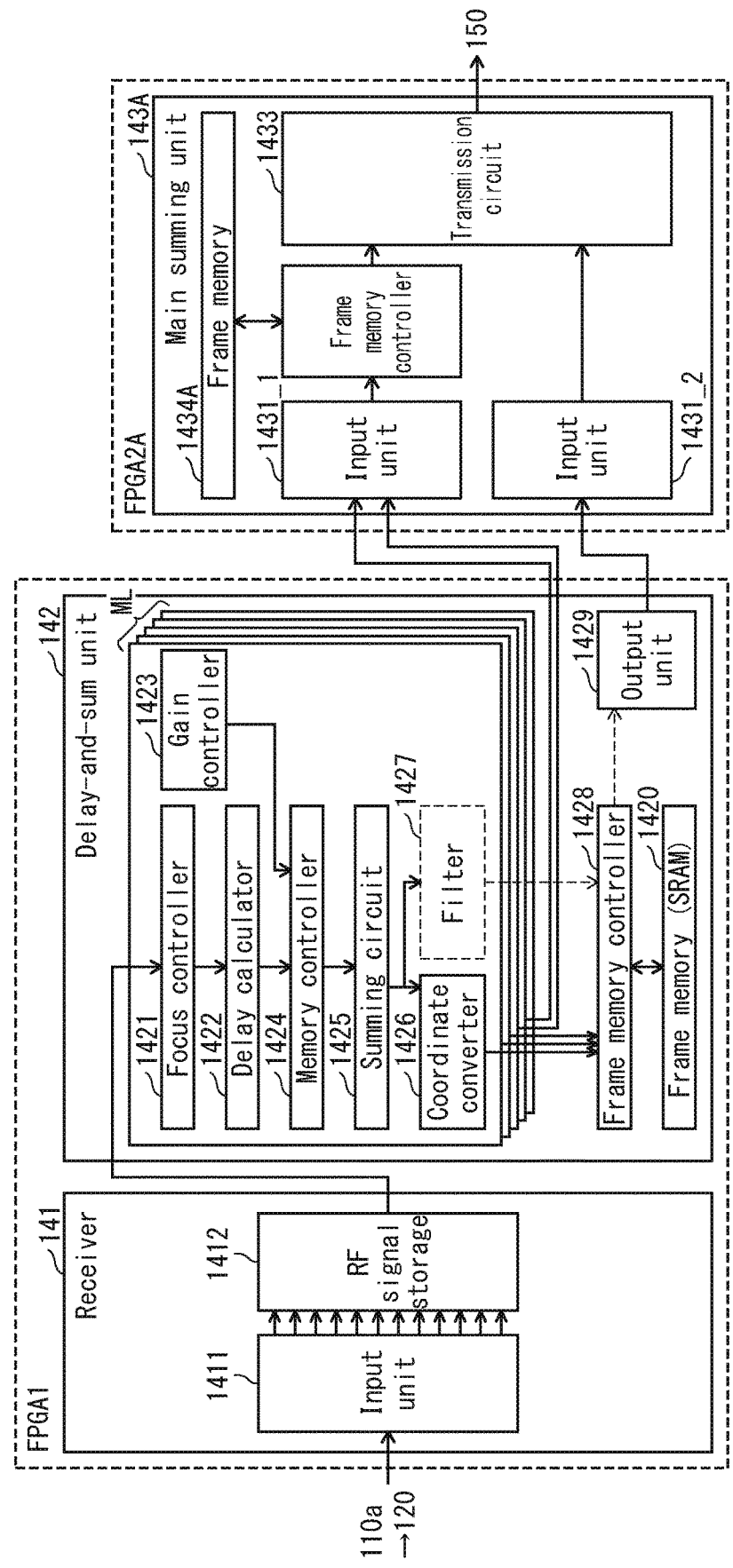
FIG. 21 is a function block diagram of a reception beamformer 140A pertaining to Modification 1.

According to a reception beamformer 140A of an ultrasound signal processing device pertaining to Modification 1, a main summing unit 143A further includes a second frame memory 1434A. FIG. 21 is a function block diagram of the reception beamformer 140A pertaining to Modification 1. According to this structure, in the first reception beamforming processing, for each transmission event, in addition to the first frame memory 1420, acoustic line signal line data can be summed for observation points at the same position written to an address in the second frame memory 1434A of the main summing unit. Further, according to Modification 1, the reception beamformer 140A can bypass the first frame memory 1420 for a portion of acoustic line signal line data generated in the delay-and-sum unit to perform summing processing in the second frame memory 1434A of the main summing unit 134A. Frame memory can be distributed among FPGA1 and FPGA2, and when compared to Embodiment 1, FPGA1 circuit modules can be reduced in cost.

<Modification 2>

Figure 22:
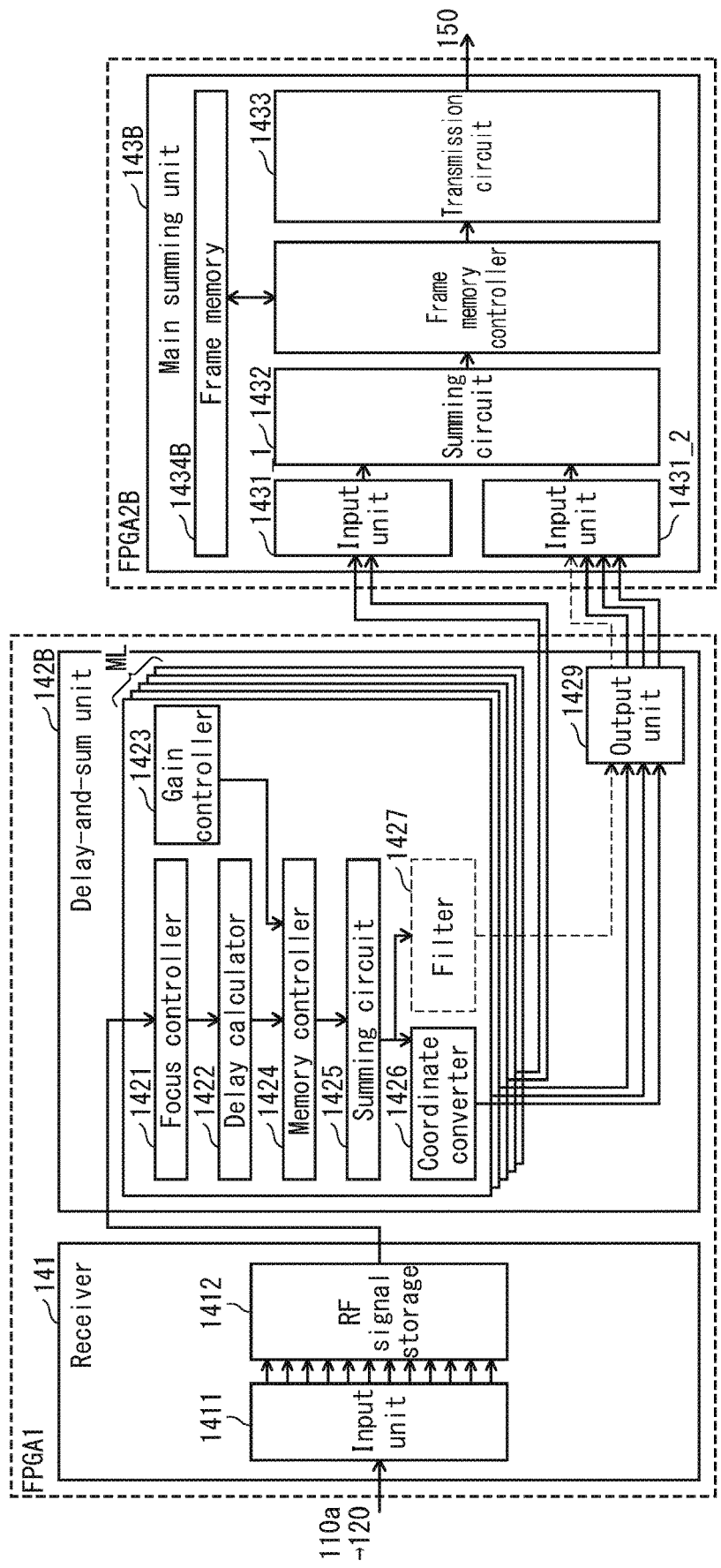
FIG. 22 is a function block diagram of a reception beamformer 140B pertaining to Modification 2.

The following describes a configuration of an ultrasound signal processing device pertaining to Modification 2. The reception beamformer 140B of the ultrasound signal processing device pertaining to Modification 2 includes a plurality of a delay-and-sum unit 142B and a main summing unit 134B that further sums acoustic line signal line data outputted from the delay-and-sum units 142B, wherein only the main summing unit 134B includes a frame memory 1434B. FIG. 22 is a function block diagram of the reception beamformer 140B pertaining to Modification 2.

More specifically, the reception beamformer 140B in the ultrasound signal processing device pertaining to Modification 2 includes the delay-and-sum unit 142B that performs delay-and-sum processing with respect to reception signal sequences of multiple channels based on reflected ultrasound to generate acoustic line signal line data, and the main summing unit 143B that sums and outputs acoustic line signal line data outputted from the delay-and-sum unit 142B. The main summing unit 143B, in the first reception beamforming processing, synthesizes and outputs acoustic line signal line data by summing acoustic line signals with respect to observation points at the same position in acoustic line signal line data calculated by the delay-and-sum unit 142B, and in the second reception beamforming processing, outputs the acoustic line signal line data calculated by the delay-and-sum unit 142B as is. The time taken to generate the acoustic line signal line data per unit number from the delay-and-sum unit 142B to the main summing unit 143B is the same or approximately the same in the first reception beamforming processing and the second reception beamforming processing.

According to this structure, in the first reception beamforming processing, for each transmission event, acoustic line signal line data can be summed with acoustic line signal data with respect to observation points at the same position written to an address corresponding to the same position in the frame memory 1434B of the main summing unit 134B. Further, according to the reception beamformer 140B of Modification 2, frame memory can be provided to different FPGA2, and cost of the circuit module of the FPGA1 can be further reduced when compared to Embodiment 1.

<<Other Modifications>>

(1) According to the ultrasound diagnostic device 100 pertaining to Embodiment 1, the focus controller 1421 selects the reception aperture Rx such that an array center coincides with the transducer having closest spatial proximity to an observation point Pij. However, configuration of the reception aperture Rx can be appropriately modified.

For example, a transmission-correlated reception aperture setting unit may be provided that selects a reception aperture Rx transducer array that has an array center that coincides with an array center of a transmission aperture Tx transducer array. According to this configuration, the reception aperture Rx transducer array is selected so that an array center of a reception aperture Rx transducer array coincides with an array center of the transmission aperture Tx transducer array. Position of a center axis of the reception aperture Rx coincides with position of a center axis of the transmission aperture Tx, and the reception aperture Rx is an aperture symmetrical about the transmission focal point F. Accordingly, position of the reception aperture Rx also shifts in correspondence with position changes of the transmission aperture Tx shifting in the array direction per transmission event.

(2) A weighting number sequence (reception apodization) with respect to each reception transducer Rk of a reception aperture Rx may be calculated so that weight of a transducer positioned on a central axis of the reception aperture Rx and a central axis of the transmission aperture Tx is a maximum, but a weighting number sequence need not be used.

(3) The ultrasound diagnostic device 100 pertaining to any embodiment is not limited to the ultrasound diagnostic device structure illustrated in FIG. 1. For example, the transmission beamformer 130 and the reception beamformer 140 may be directly connected to the transducers 110*a* of the probe 110 without the multiplexer 120. Further, the transmission beamformer 130, the reception beamformer 140, or a portion thereof may be inside the probe 110. This is not limited only to the ultrasound diagnostic device 100 pertaining to embodiments described above, and the same applies to other ultrasound diagnostic devices pertaining to embodiments described below and modifications. Further, a structure without the filter 1427 is possible.

(4) The present disclosure is based on the embodiments above, but the present disclosure is not limited to these embodiments, and the following examples are also included in the scope of the present disclosure.

For example, the present disclosure may include a computer system including a microprocessor and a memory, the memory storing a computer program and the microprocessor operating according to the computer program. For example, the present disclosure may include a computer system that operates (or instructs operation of connected elements) according to a computer program of a diagnostic method of an ultrasound diagnostic device of the present disclosure.

Further, examples in which all or part of the ultrasound diagnostic device, or all or part of a beamforming section are constituted by a computer system including a microprocessor, a storage medium such as ROM, RAM, etc., a hard disk unit, and the like, are included in the present disclosure. A computer program for achieving the same operations as the devices described above may be stored in RAM or a hard disk unit. The microprocessor operating according to the computer program, thereby realizing the functions of each device.

Further, all or part of the elements of each device may be configured as one system large scale integration (LSI). A system LSI is an ultra-multifunctional LSI manufactured by integrating a plurality of elements on one chip, and more specifically is a computer system including a microprocessor, ROM, RAM, and the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM. The microprocessor operates according to the computer program, the system LSI thereby realizing the functions. For example, a case of the beamforming method of the present disclosure stored as a program of an LSI, the LSI inserted into a computer, and a defined program (beamforming method) being executed is also included in the present disclosure.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. All or part of the functions of an ultrasound diagnostic device pertaining to at least one embodiment may be implemented by a non-transitory computer-readable storage medium on which a program is stored that causes execution of a diagnostic method or beamforming method of an ultrasound diagnostic device described above. A program and signals may be recorded and transferred on a storage medium so that the program may be executed by another independent computer system, or the program may of course be distributed via a transmission medium such as the Internet.

Alternatively, elements of the ultrasound diagnostic device pertaining to at least one embodiment may be implemented by a programmable device such as a central processing unit (CPU), a graphics processing unit (GPU), a processor, or the like, and software. This may be referred to as general-purpose computing on a graphics processing unit (GPGPU). These elements can each be a single circuit component or an assembly of circuit components. Further, a plurality of elements can be combined into a single circuit component or can be an aggregate of a plurality of circuit components.

According to the ultrasound diagnostic device pertaining to at least one embodiment, the ultrasound diagnostic device includes a data storage as a storage device. However, the storage device is not limited to this example and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integral probe and/or display.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a structure that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present disclosure is not limited to the example numbers used above.

Further, the present disclosure includes various modifications that are within the scope of conceivable ideas by a person skilled in the art.

<<Review>>

As described above, the ultrasound signal processing device pertaining to one aspect of the present disclosure is an ultrasound signal processing device comprising ultrasound signal processing circuitry, the ultrasound signal processing circuitry comprising a reception beamformer that executes processing selected from first reception beamforming processing and second reception beamforming processing. The first reception beamforming processing includes generating, for each transmission event, a set of acoustic line signal line data including acoustic line signals associated with observation points where a portion of the observation points associated with one set have a same position as a portion of the observation points associated with another set, and synthesizing acoustic line signal line data by summing acoustic line signals that are associated with the observation points having same positions. The second reception beamforming processing includes generating, for each transmission event, a set of acoustic line signal line data including one or more acoustic line signals associated with the observation points, where positions of the observation points are different for each transmission event. Numbers of lines of the acoustic line signals generated per transmission event are different between the first reception beamforming processing and the second reception beamforming processing, and the reception beamformer includes a delay-and-sum unit that performs delay-and-sum processing with respect to reception signal sequences from multiple channels based on reflected ultrasound to calculate the acoustic line signal line data. The delay-and-sum unit, in the first reception beamforming processing, synthesizes the acoustic line signal line data calculated in the delay-and-sum processing by summing the acoustic line signals associated with the observation points having the same positions, and in the second reception beamforming processing, outputs the acoustic line signal data calculated in the delay-and-sum processing as is. Time taken by the delay-and-sum unit to generate the acoustic line signal line data per set of acoustic line signal line data is equal or approximately equal in the first reception beamforming processing and the second reception beamforming processing.

According to this structure, transfer rate between circuit modules is equal or approximately equal between the first reception beamforming processing and the second reception beamforming processing, and therefore an increase in the interface specification between the delay-and-sum unit and the main summing unit, which are circuit modules in the reception beamformer, and an increase in required specification of the main summing unit, which is a subsequent stage circuit module, are suppressed.

According to at least one embodiment, the delay-and-sum unit comprises a frame memory, and in the first reception beamforming processing the delay-and-sum unit performs the synthesis by summing the acoustic line signal line data with acoustic line signals associated with the observation points having the same positions previously written to addresses of the frame memory corresponding to the positions.

According to this structure, a number of lines of acoustic line signal line data transferred to the main summing unit 143 from the delay-and-sum unit 142 in one transmission event in the first reception beamforming processing can be decreased, leading to lower cost circuitry, by performing summing processing of acoustic line signal line data in the delay-and-sum unit 142.

According to at least one embodiment, the reception beamformer comprises a plurality of the delay-and-sum unit, and a main summing unit that further sums acoustic line signal line data outputted from the plurality of the delay-and-sum unit.

According to this structure, it is possible to configure a multi-channel reception beamforming circuit using a plurality of circuit modules including the delay-and-sum unit 142. The main summing unit can be made with only a simple summing circuit and a DMA transfer circuit.

According to at least one embodiment, the main summing unit further comprises a second frame memory.

According to this structure, prior stage circuit module cost can be reduced.

According to at least one embodiment, the number of lines of the acoustic line signal line data outputted by the delay-and-sum unit per transmission event is ML in the first reception beamforming processing, and NL in the second reception beamforming processing, and a maximum value of ML and NL is max(ML, NL), and the delay-and-sum unit, in processing generating and outputting max(ML, NL) lines of the acoustic line signal line data, generates and outputs the max(ML, NL) lines of the acoustic line signal line data in a max(ML, NL) cycle time slot period by operating at a max(ML, NL) multiple of processing speed.

According to this structure, it is possible to generate acoustic line signal line data within the same time slots in both the first reception beamforming processing and the second reception beamforming processing.

According to at least one embodiment, a minimum value of ML and NL is min(ML, NL), and the delay and sum unit, in processing generating and outputting min(ML, NL) lines of the acoustic line signal line data, stops generation and output of the acoustic line signal line data in a (max(ML, NL)−min(ML, NL)) cycle time slot period.

According to this structure, by performing time-division processing (time slot processing) of max(ML,NL) double-speed operations, scalable processing becomes possible and circuit structure can be simplified.

According to at least one embodiment, the ultrasound signal processing device comprises ultrasound signal processing circuitry, the ultrasound signal processing circuitry comprising a reception beamformer and a main summing unit. The reception beamformer executes processing selected from first reception beamforming processing and second reception beamforming processing. The first reception beamforming processing includes generating a set of acoustic line signal line data including acoustic line signals associated with observation points for each transmission event, where a portion of the observation points associated with one set have a same position as a portion of the observation points associated with another set, and synthesizing acoustic line signal line data by summing acoustic line signals that are associated with the observation points having same positions. The second reception beamforming processing includes generating a set of acoustic line signal line data including one or more acoustic line signals associated with the observation points for each transmission event, where positions of the observation points are different for each transmission event. Numbers of lines of the acoustic line signals generated per transmission event are different between the first reception beamforming processing and the second reception beamforming processing. The reception beamformer includes a delay-and-sum unit that performs delay-and-sum processing with respect to reception signal sequences from multiple channels based on reflected ultrasound to calculate the acoustic line signal line data. The main summing unit sums and outputs the acoustic line signal line data outputted from the delay-and-sum unit. The main summing unit, in the first reception beamforming processing, synthesizes the acoustic line signal line data calculated by the delay-and-sum unit by summing the acoustic line signals associated with the observation points having the same positions, and in the second reception beamforming processing, outputs the acoustic line signal data calculated by the delay-and-sum unit as is. Time taken by the delay-and-sum unit to generate the acoustic line signal line data per set of acoustic line signal line data is equal or approximately equal in the first reception beamforming processing and the second reception beamforming processing.

According to at least one embodiment, the main summing unit comprises a frame memory, and in the first reception beamforming processing the main summing unit performs the synthesis by summing the acoustic line signal line data with acoustic line signals associated with the observation points having the same positions previously written to addresses of the frame memory corresponding to the positions.

According to this structure, prior stage circuit module cost can be further reduced.

According to at least one embodiment, the transmission event comprises transmitting an ultrasound beam to a target region in a subject from a transmission transducer array selected from transducers arrayed on an ultrasound probe, the reflected ultrasound is received by the transducers, and the reception signal sequences are obtained by executing the transmission event multiple times while gradually shifting the transmission transducer array in an array direction. In the first reception beamforming processing, the delay-and-sum unit performs the delay-and-sum processing with respect to the observation points positioned on first virtual lines extending in a depth direction of the subject from the transmission transducer array, wherein positions of a portion of the observation points on the first virtual lines of consecutive transmission events coincide. In the second reception beamforming processing, the delay-and-sum unit performs the delay-and-sum processing with respect to the observation points positioned on second virtual lines extending in the depth direction of the subject from the transmission transducer array, wherein positions of the observation points on the second virtual lines of consecutive transmission events do not coincide.

According to this structure, the first reception beamforming processing by a synthetic aperture method and the second reception beamforming processing by a simple delay-and-sum method become possible.

According to at least one embodiment, in the second reception beamforming processing, the acoustic line signal line data is outputted without being written to the frame memory.

According to this structure, both delay-and-sum beamforming processing and synthetic aperture beamforming processing functions can be cheaply implemented by a structure in which transfer rates between circuit modules are equal or approximately equal.

As described above, according to an ultrasound signal processing device and an ultrasound diagnostic device that makes use of the ultrasound signal processing device pertaining to at least one embodiment of the present disclosure, between first reception beamforming processing by a synthetic aperture method and second reception beamforming processing by a simple delay-and-sum method, both delay-and-sum beamforming processing and synthetic aperture beamforming processing functions can be cheaply implemented in reception beamforming circuitry by a structure in which transfer rates between circuit modules are equal or approximately equal.

Thus, the ultrasound signal processing device, the ultrasound diagnostic device, the ultrasound signal processing method, the program, and the computer-readable non-transitory storage medium pertaining to the present disclosure are effective in improving functionality of conventional ultrasound diagnostic devices, in particular reducing costs of calculators in reception beamformers using a synthetic aperture method and improving frame rate by reducing calculation load and data transfer load. Further, the present disclosure can be applied not only to ultrasound, but also to applications such as sensors that use a plurality of array elements.

<<Supplement>>

The embodiments described above each indicate one preferred specific example of the present disclosure. Numerical values, shapes, materials, constituent elements, arrangement positions and connections of constituent elements, steps, order of steps, and the like indicated as embodiments are merely examples and are not intended to limit the present disclosure. Further, among constituent elements in the embodiments, elements not described in independent claims representing top level concepts of the present disclosure are described as any constituent element constituting a more beneficial embodiment.

Further, the order in which steps described above are executed is for illustrative purposes, and the steps may be in an order other than described above. Further, a portion of the steps described above may be executed simultaneously (in parallel) with another step.

Further, in order to facilitate understanding, constituent elements in each drawing referenced by description of an embodiment are not necessarily to scale. Further, the present disclosure is not limited by the description of each embodiment and can be appropriately changed without departing from the scope of the present disclosure.

Although the technology pertaining to the present disclosure has been fully described by way of examples with reference to the accompanying drawings, various changes and modifications will be apparent to those skilled in the art. Therefore, unless such changes and modifications depart from the scope of the present disclosure, they should be construed as being included herein.

What is claimed is:

1. An ultrasound signal processing device comprising ultrasound signal processing circuitry, the ultrasound signal processing circuitry comprising
   a reception beamformer configured to execute processings of a first reception beamforming processing and a second reception beamforming processing, wherein
      the first reception beamforming processing includes generating, for each transmission event, a set of acoustic line signal line data including acoustic line signals from electrical signals obtained from transducers based on reflected ultrasound associated with observation points where a portion of the observation points associated with one set have a same position as a portion of the observation points associated with another set, and synthesizing acoustic line signal line data by summing acoustic line signals that are associated with the observation points having same positions, and
      the second reception beamforming processing includes generating, for each transmission event, a set of acoustic line signal line data including one or more acoustic line signals from electrical signals obtained from transducers based on reflected ultrasound associated with the observation points,
   where positions of the observation points are different for each transmission event, wherein numbers of lines of the acoustic line signals generated per transmission event are different between the first reception beamforming processing and the second reception beamforming processing, and the reception beamformer includes a delay-and-sum unit configured to perform delay-and-sum processing with respect to reception signal sequences from multiple channels based on reflected ultrasound to calculate the acoustic line signal line data, the delay-and-sum unit including common circuit module elements, at least one first circuit module element, and at least one second circuit module element, and the delay-and-sum unit further configured to perform,
  in the first reception beamforming processing, synthesizing the acoustic line signal line data calculated in the delay-and-sum processing by summing the acoustic line signals associated with the observation points having the same positions by causing operation of the common circuit module elements and the at least one first circuit module element, and
  in the second reception beamforming processing, outputting the acoustic line signal data calculated in the delay-and-sum processing as is without performing any synthesizing of the acoustic line signal line data by causing operation of the common circuit module elements and the at least one second circuit module element, and
transfer rates of the acoustic line signal line data by the delay-and-sum unit in the first reception beamforming processing and the second reception beamforming processing are equal or closely approximated.

2. The ultrasound signal processing device of claim 1, wherein the delay-and-sum unit comprises a frame memory, in the first reception beamforming processing the delay-and-sum unit performs the synthesis by summing the acoustic line signal line data with acoustic line signals associated with the observation points having the same positions previously written to addresses of the frame memory corresponding to the positions, and in the second reception beamforming processing the delay-and-sum unit outputs the acoustic line signal line data in the order the acoustic line signal line data is generated without storing the acoustic line signal line data in the frame memory.

3. The ultrasound signal processing device of claim 2, wherein the reception beamformer comprises a plurality of the delay-and-sum unit, and a main summing unit that further sums acoustic line signal line data outputted from the plurality of the delay-and-sum unit.

4. The ultrasound signal processing device of claim 3, wherein the main summing unit further comprises a second frame memory.

5. The ultrasound signal processing device of claim 1, wherein
  the number of lines of the acoustic line signal line data outputted by the delay-and-sum unit per transmission event is ML in the first reception beamforming processing, and NL in the second reception beamforming processing, and a maximum value of ML and NL is max(ML, NL), and
  the delay-and-sum unit, in processing generating and outputting max(ML, NL) lines of the acoustic line signal line data, generates and outputs the max(ML, NL) lines of the acoustic line signal line data in a max(ML, NL) cycle time slot period by operating at a max(ML, NL) multiple of processing speed.

6. The ultrasound signal processing device of claim 5, wherein
  a minimum value of ML and NL is min(ML, NL), and
  the delay-and-sum unit, in processing generating and outputting min(ML, NL) lines of the acoustic line signal line data, stops generation and output of the acoustic line signal line data in a (max(ML, NL)−min(ML, NL)) cycle time slot period.

7. An ultrasound signal processing device comprising ultrasound signal processing circuitry, the ultrasound signal processing circuitry comprising:
  a reception beamformer configured to execute processings of a first reception beamforming processing and a second reception beamforming processing, wherein
    the first reception beamforming processing includes generating a set of acoustic line signal line data including acoustic line signals from electrical signals obtained from transducers based on reflected ultrasound associated with observation points for each transmission event, where a portion of the observation points associated with one set have a same position as a portion of the observation points associated with another set, and synthesizing acoustic line signal line data by summing acoustic line signals that are associated with the observation points having same positions, and
    the second reception beamforming processing includes generating a set of acoustic line signal line data including one or more acoustic line signals from electrical signals obtained from transducers based on reflected ultrasound associated with the observation points for each transmission event, where positions of the observation points are different for each transmission event,
  wherein numbers of lines of the acoustic line signals generated per transmission event are different between the first reception beamforming processing and the second reception beamforming processing, and
  the reception beamformer includes a delay-and-sum unit configured to perform delay-and-sum processing with respect to reception signal sequences from multiple channels based on reflected ultrasound to calculate the acoustic line signal line data, the delay-and-sum unit including common circuit module elements, at least one first circuit module element, and at least one second circuit module element; and
  a main summing unit configured to perform sum and output the acoustic line signal line data outputted from the delay-and-sum unit,
  wherein the main summing unit is further configured to perform,
    in the first reception beamforming processing, synthesizing the acoustic line signal line data calculated by the delay-and-sum unit by summing the acoustic line signals associated with the observation points having the same positions by causing operation of the common circuit module elements and the at least one first circuit module element, and
    in the second reception beamforming processing, outputting the acoustic line signal data calculated by the delay-and-sum unit as is without performing any synthesizing of the acoustic line signal line data by causing operation of the common circuit module elements and the at least one second circuit module element, and
  transfer rates of the acoustic line signal line data by the delay-and-sum unit in the first reception beamforming processing and the second reception beamforming processing are equal or closely approximated.

8. The ultrasound signal processing device of claim 7, wherein
the number of lines of the acoustic line signal line data outputted by the delay-and-sum unit per transmission event is ML in the first reception beamforming processing, and NL in the second reception beamforming processing, and a maximum value of ML and NL is max(ML, NL), and
the delay-and-sum unit, in processing generating and outputting max(ML, NL) lines of the acoustic line signal line data, generates and outputs the max(ML, NL) lines of the acoustic line signal line data in a max(ML, NL) cycle time slot period by operating at a max(ML, NL) multiple of processing speed.

9. The ultrasound signal processing device of claim 8, wherein
a minimum value of ML and NL is min(ML, NL), and
the delay-and-sum unit, in processing generating and outputting min(ML, NL) lines of the acoustic line signal line data, stops generation and output of the acoustic line signal line data in a (max(ML, NL)−min(ML, NL)) cycle time slot period.

10. The ultrasound signal processing device of claim 7, wherein the main summing unit comprises a frame memory, in the first reception beamforming processing the main summing unit performs the synthesis by summing the acoustic line signal line data with acoustic line signals associated with the observation points having the same positions previously written to addresses of the frame memory corresponding to the positions, and in the second reception beamforming processing the main summing unit outputs the acoustic line signal line data in the order the acoustic line signal line data is generated without storing the acoustic line signal line data in the frame memory.

11. The ultrasound signal processing device of claim 1, wherein
the transmission event comprises transmitting an ultrasound beam to a target region in a subject from a transmission transducer array selected from transducers arrayed on an ultrasound probe, the reflected ultrasound is received by the transducers, and the reception signal sequences are obtained by executing the transmission event multiple times while gradually shifting the transmission transducer array in an array direction,
in the first reception beamforming processing, the delay-and-sum unit performs the delay-and-sum processing with respect to the observation points positioned on first virtual lines extending in a depth direction of the subject from the transmission transducer array, wherein positions of a portion of the observation points on the first virtual lines of consecutive transmission events coincide,
in the second reception beamforming processing, the delay-and-sum unit performs the delay-and-sum processing with respect to the observation points positioned on second virtual lines extending in the depth direction of the subject from the transmission transducer array, wherein positions of the observation points on the second virtual lines of consecutive transmission events do not coincide.

12. An ultrasound image diagnostic device comprising:
an ultrasound probe that includes a plurality of transducers; and
an ultrasound signal processing device comprising ultrasound signal processing circuitry, the ultrasound signal processing circuitry comprising
a reception beamformer configured to execute processings of a first reception beamforming processing and a second reception beamforming processing with respect to reception signal sequences from the ultrasound probe, wherein
the first reception beamforming processing includes generating, for each transmission event, a set of acoustic line signal line data including acoustic line signals from electrical signals obtained from transducers based on reflected ultrasound associated with observation points where a portion of the observation points associated with one set have a same position as a portion of the observation points associated with another set, and synthesizing acoustic line signal line data by summing acoustic line signals that are associated with the observation points having same positions, and
the second reception beamforming processing includes generating, for each transmission event, a set of acoustic line signal line data including one or more acoustic line signals from electrical signals obtained from transducers based on reflected ultrasound associated with the observation points, where positions of the observation points are different for each transmission event,
wherein numbers of lines of the acoustic line signals generated per transmission event are different between the first reception beamforming processing and the second reception beamforming processing, and
the reception beamformer includes a delay-and-sum unit configured to perform delay-and-sum processing with respect to the reception signal sequences from multiple channels based on reflected ultrasound to calculate the acoustic line signal line data, the delay-and-sum unit including common circuit module elements, at least one first circuit module element, and at least one second circuit module element, and
the delay-and-sum unit is further configured to perform,
in the first reception beamforming processing, synthesizing the acoustic line signal line data calculated in the delay-and-sum processing by summing the acoustic line signals associated with the observation points having the same positions by causing operation of the common circuit module elements and the at least one first circuit module element, and
in the second reception beamforming processing, outputting the acoustic line signal data calculated in the delay-and-sum processing as is without performing any synthesizing of the acoustic line signal line data by causing operation of the common circuit module elements and the at least one second circuit module element, and
transfer rates of the acoustic line signal line data by the delay-and-sum unit in the first reception beamforming processing and the second reception beamforming processing are equal or closely approximated.

13. The ultrasound signal processing device of claim 1, wherein the delay-and-sum unit generates and processes the set of of acoustic line signal line data in the first reception beamforming processing in M cycle time slot periods and generates and processes the set of acoustic line signals in the second reception beamforming processing in N cycle time slot periods, and
in processing generating and outputting the number of lines of the acoustic line signal line data for the second reception beamforming processing, the delay-and-sum unit stops generation and output of the acoustic line signal line data in M-N cycle time slot periods so that the time taken by the delay-and-sum unit to generate the acoustic line signal line data per set of acoustic line signal line data is equal or approximately equal in the first reception beamforming processing and the second reception beamforming processing.

* * * * *